US009827321B2

(12) United States Patent
Burdick et al.

(10) Patent No.: US 9,827,321 B2
(45) Date of Patent: Nov. 28, 2017

(54) STABILIZING SHEAR-THINNING HYDROGELS

(71) Applicant: The Trustees of The University of Pennsylvania, Philadelphia, PA (US)

(72) Inventors: Jason A. Burdick, Philadelphia, PA (US); Christopher B. Rodell, Peachtree City, GA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 37 days.

(21) Appl. No.: 14/420,787

(22) PCT Filed: Jul. 30, 2013

(86) PCT No.: PCT/US2013/052641
§ 371 (c)(1),
(2) Date: Feb. 10, 2015

(87) PCT Pub. No.: WO2014/028209
PCT Pub. Date: Feb. 20, 2014

(65) Prior Publication Data
US 2015/0202299 A1    Jul. 23, 2015

Related U.S. Application Data

(60) Provisional application No. 61/682,926, filed on Aug. 14, 2012.

(51) Int. Cl.
| | |
|---|---|
| *A61L 31/04* | (2006.01) |
| *A61L 31/14* | (2006.01) |
| *A61K 47/36* | (2006.01) |
| *A61L 31/16* | (2006.01) |
| *A61K 9/00* | (2006.01) |
| *A61K 9/06* | (2006.01) |
| *A61K 35/00* | (2006.01) |
| *A61K 38/20* | (2006.01) |
| *A61K 47/40* | (2006.01) |
| *A61K 47/42* | (2017.01) |

(52) U.S. Cl.
CPC ............ *A61K 47/36* (2013.01); *A61K 9/0024* (2013.01); *A61K 9/06* (2013.01); *A61K 35/00* (2013.01); *A61K 38/2066* (2013.01); *A61K 47/40* (2013.01); *A61K 47/42* (2013.01); *A61L 31/042* (2013.01); *A61L 31/145* (2013.01); *A61L 31/16* (2013.01); *A61L 2300/64* (2013.01)

(58) Field of Classification Search
CPC .... A61K 31/145; A61K 9/0024; A61K 47/36; A61K 47/40; A61K 35/00
See application file for complete search history.

(56) References Cited

U.S. PATENT DOCUMENTS

| | | |
|---|---|---|
| 6,080,450 A | 6/2000 | Cantor |
| 6,790,840 B1 | 9/2004 | Lee et al. |
| 7,074,424 B2 | 7/2006 | Avila et al. |
| 7,191,456 B2 | 3/2007 | Guo |
| 7,297,348 B2 | 11/2007 | Li et al. |
| 7,375,096 B1 | 5/2008 | Davis et al. |
| 7,376,996 B2 | 5/2008 | Landi et al. |
| 7,520,091 B2 | 4/2009 | Friedman |
| 7,767,656 B2 | 8/2010 | Shoichet et al. |
| 7,829,109 B2 | 11/2010 | Chen et al. |
| 7,858,585 B2 | 12/2010 | Ozbas et al. |
| 7,968,110 B2 | 6/2011 | Hubbard |
| 7,968,123 B2 | 6/2011 | Pun et al. |
| 8,003,125 B2 | 8/2011 | Li et al. |
| 8,017,688 B2 | 9/2011 | Ito et al. |
| 8,038,991 B1 | 10/2011 | Stankus et al. |
| 8,110,561 B2 | 2/2012 | Cohen et al. |
| 8,288,362 B2 | 10/2012 | Karageozian et al. |
| 8,314,230 B2 | 11/2012 | Cheng et al. |
| 8,357,377 B2 | 1/2013 | Pun et al. |
| 8,383,158 B2 | 2/2013 | Michal et al. |
| 2005/0271727 A1 | 12/2005 | Yao |
| 2008/0132600 A1 | 6/2008 | Nesvadba et al. |
| 2008/0193536 A1 | 8/2008 | Khademhosseini et al. |
| 2009/0269323 A1 | 10/2009 | Luk et al. |
| 2011/0189140 A1 | 8/2011 | Christman et al. |
| 2012/0156250 A1 | 6/2012 | Christman et al. |

FOREIGN PATENT DOCUMENTS

WO    WO 2014-028209    2/2014

OTHER PUBLICATIONS

Anderson et al, "A Combinatorial Library of Photocrosslinkable and Degradable Materials", Adv. Mater. Sep. 14, 2006, 18, 2614-2618.
Appeal et al, "Supermolecular Cross-Linked Networks via Host-Guest Complexation with Cucurbit[8]uril", J. Am. Chem. Soc., Sep. 2010, 132, 14251-14260.
Chariot, A. and Auze'ly-Velty, R., "Novel Hyaluronic Acid Based Supramolecular Assemblies Stabilized by Multivalent Specific Interactions: Rheological Behavior in Aqueous Solution", Macromolecules, Dec. 2007, 40, 9555-9563.
Chen, G. and Jiang, M., "Cyclodextrin-based Inclusion Complexation Bridging Supramolecular Chemistry and Macromolecular Self-Assembly", Chem. Soc. Rev., Feb. 2011, 40, 2254-2266.
Guvendiren et al. "Shear-Thinning Hydrogels for Biomedical Applications", Soft Matter, 2012, 8, 260-272, Published Online: Oct. 17, 2011.

(Continued)

*Primary Examiner* — Gina Justice
(74) *Attorney, Agent, or Firm* — Baker & Hostetler LLP

(57) ABSTRACT

The present inventions are directed to shear-thinning and stabilizing hydrogels, especially for use in drug delivery and therapy. Various embodiments provide settable, shear-thinning hydrogels, each hydrogel comprising a hydrophilic polymer network, said hydrophilic polymer network comprising non-covalent crosslinks and at least one set of chemical moieties being capable of participating in at least one chemical covalent cross-linking reaction. In certain embodiments, these settable shear-thinning hydrogels are triggerable to cross-link by the application of a stimulus.

38 Claims, 16 Drawing Sheets

(56) References Cited

OTHER PUBLICATIONS

International Application No. PCT/US13/52641: International Search Report and Written Opinion dated Jan. 24, 2014, 17 pages.

Kaya et al, "Synthesis and Characterization of Physical Crosslinking Systems Based on Cyclodextrin Inclusion/Host-Guest Complexation", Journal of Polymer Science Part A: Polymer Chemistry, Feb. 1, 2010, 48(3), 581-592.

Lu et al, "Injectable Shear-Thinning Hydrogels Engineered With a Self-Assembling Dock-and-Lock Mechanism", Biomaterials, Mar. 2012, 33(7), 2145-2153.

Park et al, "In Situ Supramolecular Assembly and Modular Modification of Hyaluronic Acid Hydrogels for 3D Cellular Engineering", ACSNano, Mar. 12, 2012, 6(4), 2960-2968.

Studier, F.W., "Protein Production by Auto-Induction in High-Density Shaking Cultures", Protein Expression and Purification, May 2005, 41(1), 207-234.

Tan et al, "Electrospinning of Photocrosslinked and Degradable Fibrous Scaffolds", Dec. 15, 2008, 87A(4), 1034-1043.

Tous et al, "Influence of Injectable Hyaluronic Acid Hydrogel Degradation Behavior on Infarction Induced Ventricular Remodeling", Biomacromolecules, Oct. 3, 2011, 12(11), 4127-4135.

Yu et al, "Investigation of the Interactions Between the Hydrophobic Cavities of Cyclodetrins and Pullulanase", Molecules, Apr. 7, 2011, 16, 3010-3017.

FIG. 3A, C
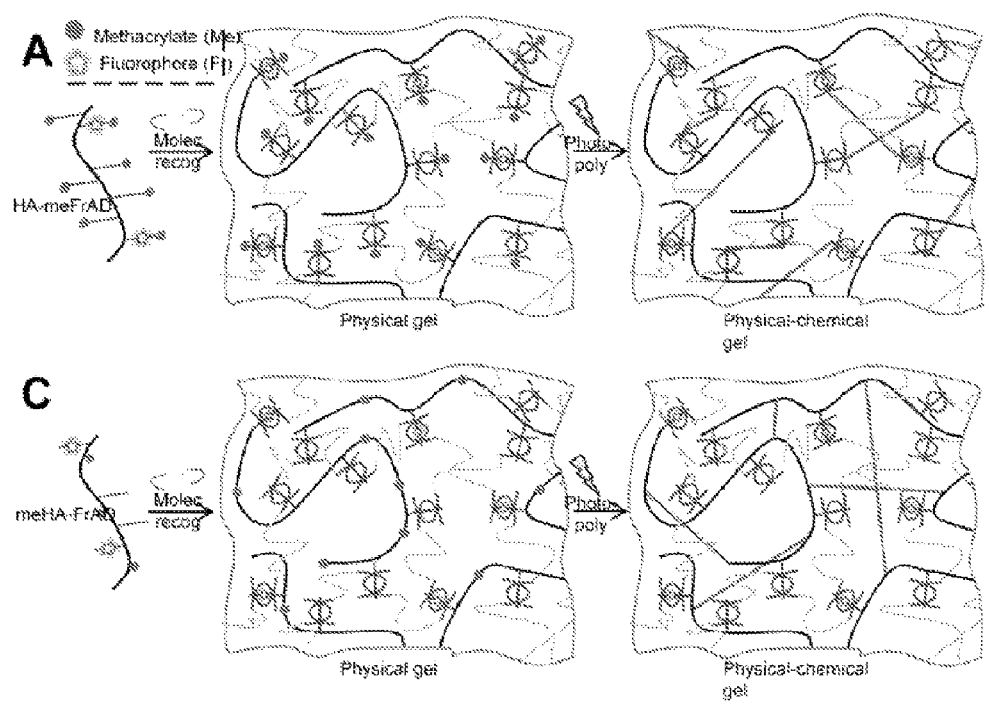

FIG. 3B, D
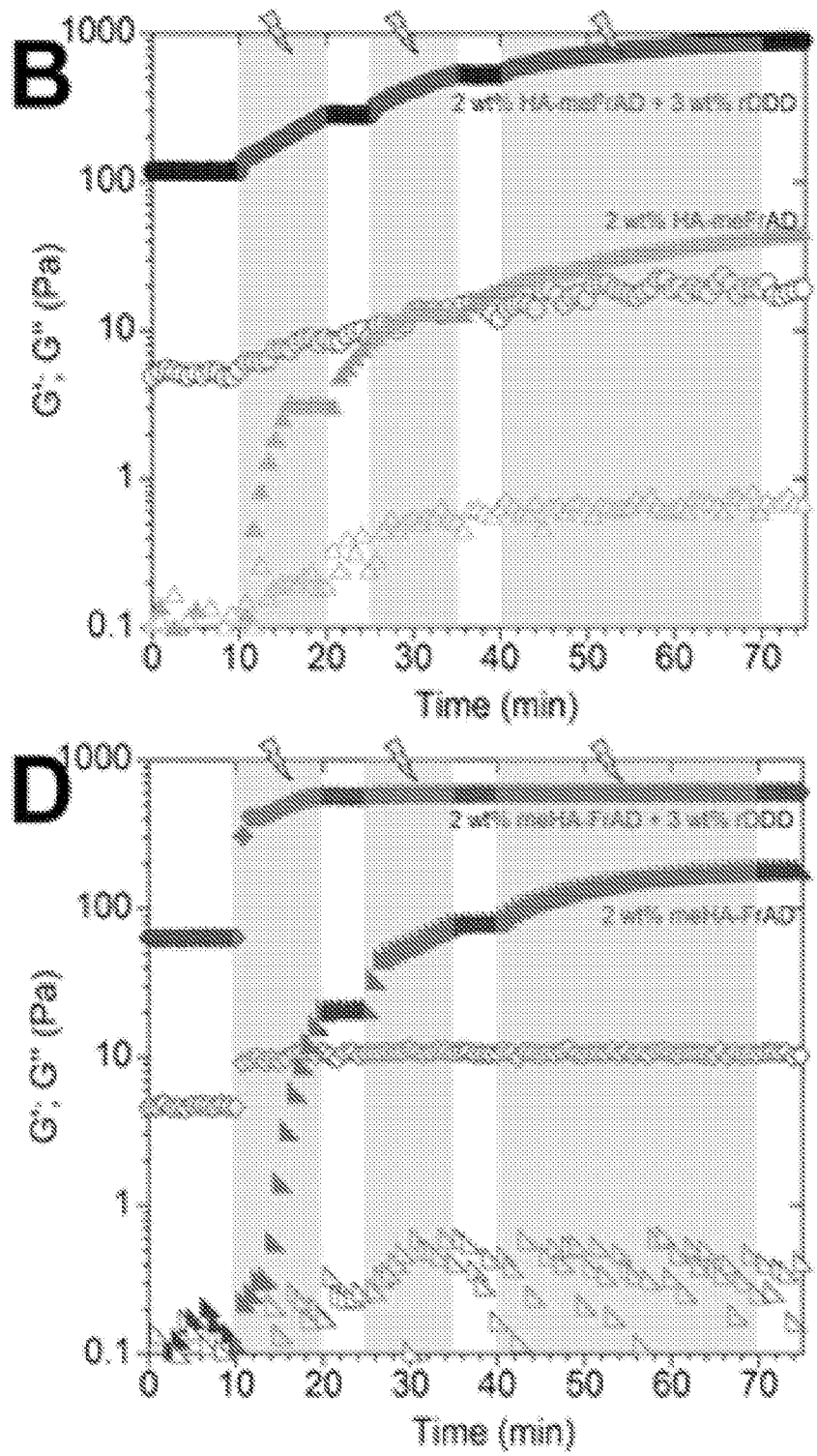

FIG. 6 A, C
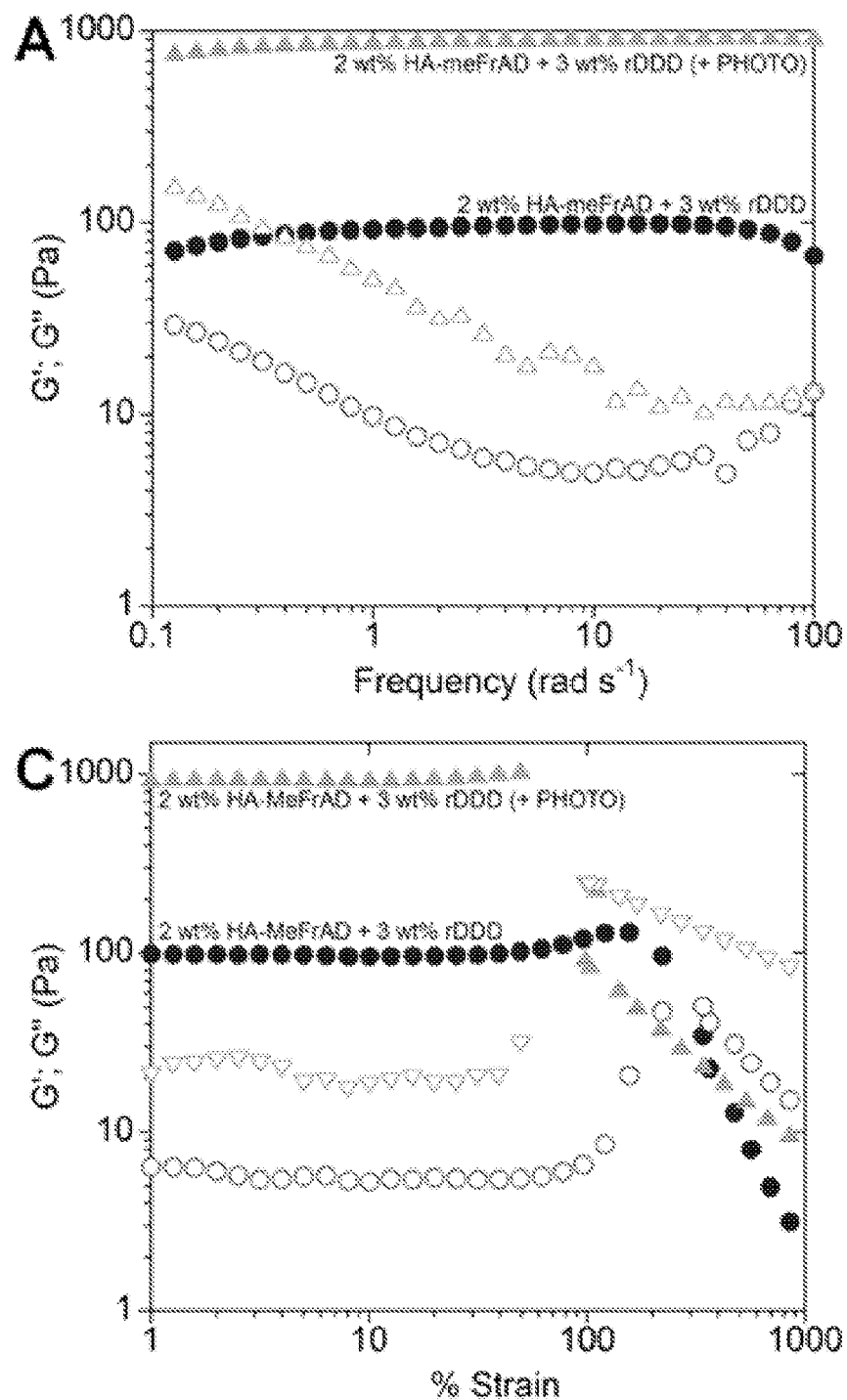

FIG. 6 B, D
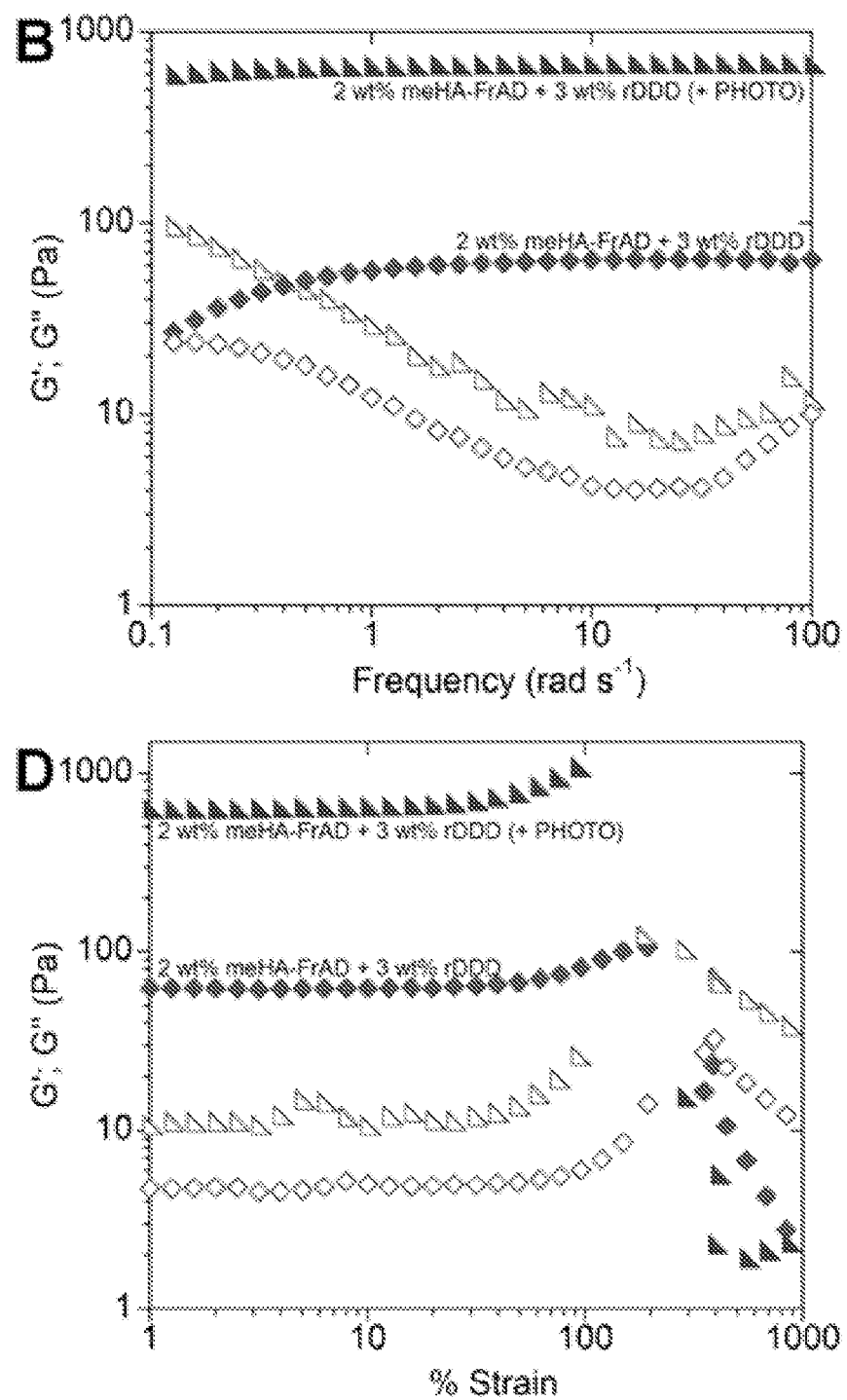

FIG. 7
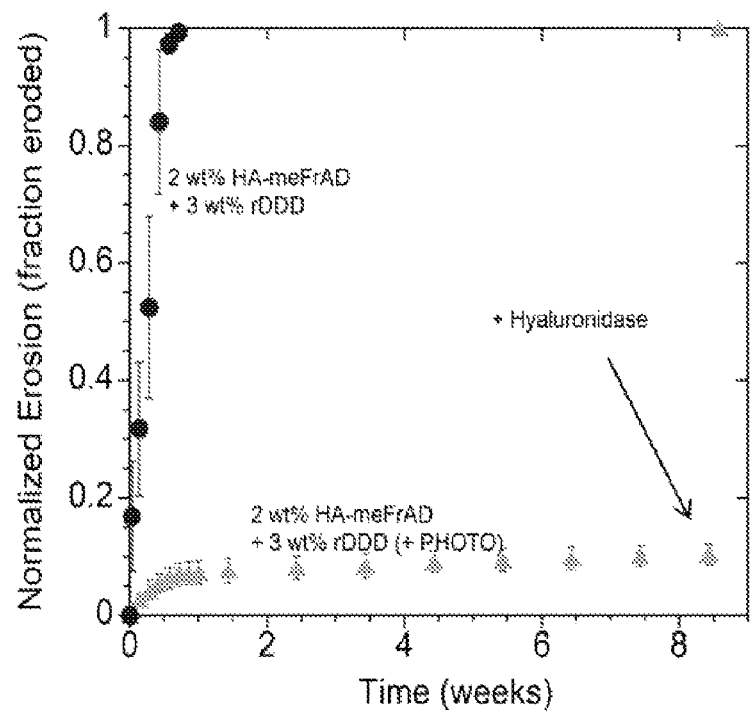
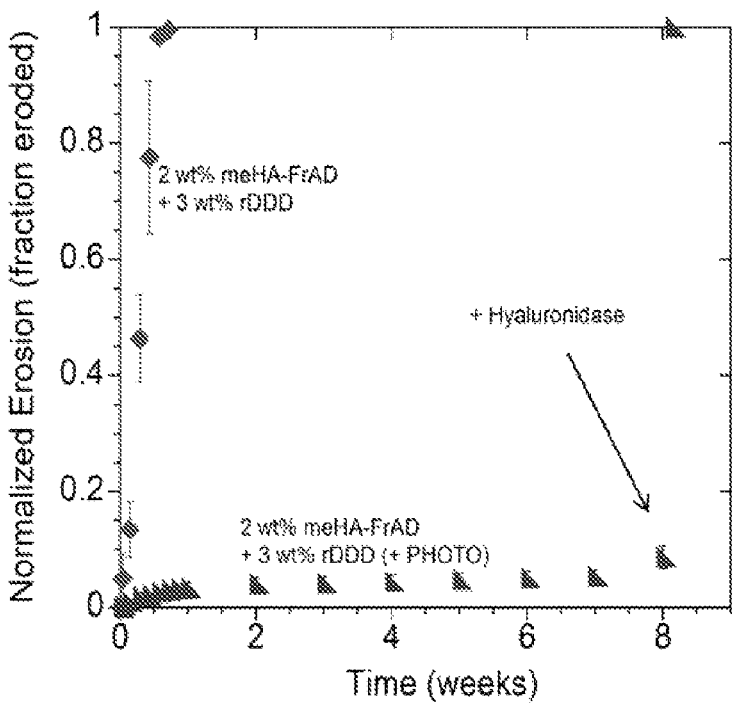

Primary Guest-Host Cross-linking

Secondary Covalent Cross-linking

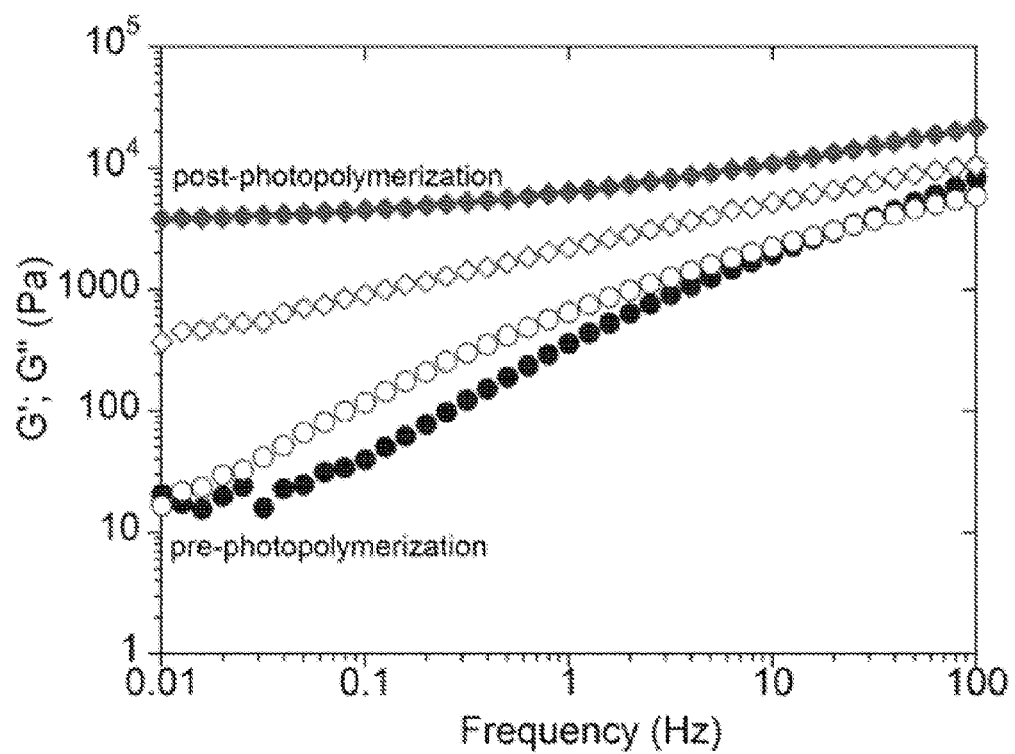

STABILIZING SHEAR-THINNING HYDROGELS

CROSS REFERENCE TO RELATED APPLICATIONS

This application is the National Stage of International Application No. PCT/US2013/052641 filed Jul. 30, 2013, which claims the benefit of and priority to U.S. provisional Application No. 61/682,926, filed Aug. 14, 2012, the entireties of which applications are incorporated herein by reference for any and all purposes.

TECHNICAL FIELD

The present inventions are directed to stabilizing shear-thinning hydrogels, especially for use in drug delivery and therapy.

BACKGROUND

Hydrogels can enhance cell and drug therapies by modulating encapsulated cell and drug activity. Injectable hydrogels are particularly relevant in clinical settings since they may be implanted with minimally invasive methods and with minimal prior knowledge of defect site geometry.

Current shear-thinning and injectable hydrogel systems are known to suffer from problems of instability after delivery, described in the literature as bio-erosion, where the gel structures break down with time owing to the longer-term instability of the non-covalent nature of the crosslinking within the shear thinning hydrogels.

SUMMARY

The present invention(s) are directed to stabilizing shear-thinning hydrogels.

Various embodiments provide settable, shear-thinning hydrogels, each hydrogel comprising a hydrophilic polymer network, said hydrophilic polymer network comprising non-covalent crosslinks and at least one set of chemical moieties being capable of participating in at least one chemical covalent cross-linking reaction. In certain embodiments, these settable shear-thinning hydrogels are triggerable to cross-link by the application of a stimulus.

Other embodiments are directed to cured hydrogels, where the chemical moieties within the settable, shear-thinning hydrogels capable of participating have undergone at least one reaction to provide at least one chemical covalent cross-linking within the matrix.

In certain of these embodiments, the settable, shear-thinning hydrogel and/or the cured hydrogel further comprises a pharmaceutically active drug or neutraceutical, a population of cells, nanoparticle, quantum dot, magnetic material, or combination thereof.

In other embodiments, the settable, shear-thinning hydrogel and/or the cured hydrogel is adapted to be medically acceptable for use in a mammal, for example, a human.

Other embodiments provide methods of preparing controlled or sustained release formulations of a pharmaceutically active drug, neutraceutical, or cell population in a patient, each method comprising introducing into the patient a composition comprising a settable, shear-thinning hydrogel and a pharmaceutically active drug, neutraceutical, or cell population. Still other embodiments provide methods of preparing a controlled or sustained release formulation of a pharmaceutically active drug, neutraceutical, or cell population in a patient, each method comprising introducing into a patient the composition comprising: (a) a settable shear-thinning hydrogel comprising a network hydrophilic polymers, said hydrophilic polymers comprising non-covalent linkages, and further comprising at least one set of chemical moieties being capable of participating in at least one chemical covalent cross-linking reaction; and (b) a pharmaceutically active drug, neutraceutical, or cell population. Further embodiments further comprise triggering at least one chemical covalent crosslinking reaction.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 3 provides design schematic of DnL hydrogels with methacrylate pendants on the AD peptide (FIG. 3A) and hyaluronic acid (HA) backbone (FIG. 3C). FIG. 3B and FIG. 3D provide data for timesweeps of methacrylated DnL components and gels upon photopolymerization. Rheology experiments were performed at 1% deformation strain and 6.3 rad $s^{-1}$ with 13 mW/cm$^2$ irradiation at 470 nm.

FIG. 6 provides frequency (FIG. 6 A-B) and strain sweep (FIG. 6 C-D) data of pre- and post-photo-polymerized DnL hydrogels. Experiments were performed at 1% strain, 6.3 rad $s^{-1}$ with 13 mW/cm$^2$ irradiation at 470 nm wavelength.

FIGS. 7A-B illustrate the improvements in bioerosion available in photopolymerizing to crosslink an acrylate-modified a DnL hydrogel, as described in Example 1.

FIG. 9 provides a schematic representation of the non-covalent bonding associated with guest-host hydrogels, wherein the polymers comprising the hydrogel are shown to contain sets of chemical moieties (in this case, methacrylate vinyl groups) capable of forming chemical covalent cross-links on application of an external stimulus.

(FIGS. 10 B-C).

DETAILED DESCRIPTION OF ILLUSTRATIVE EMBODIMENTS

Figure 1:
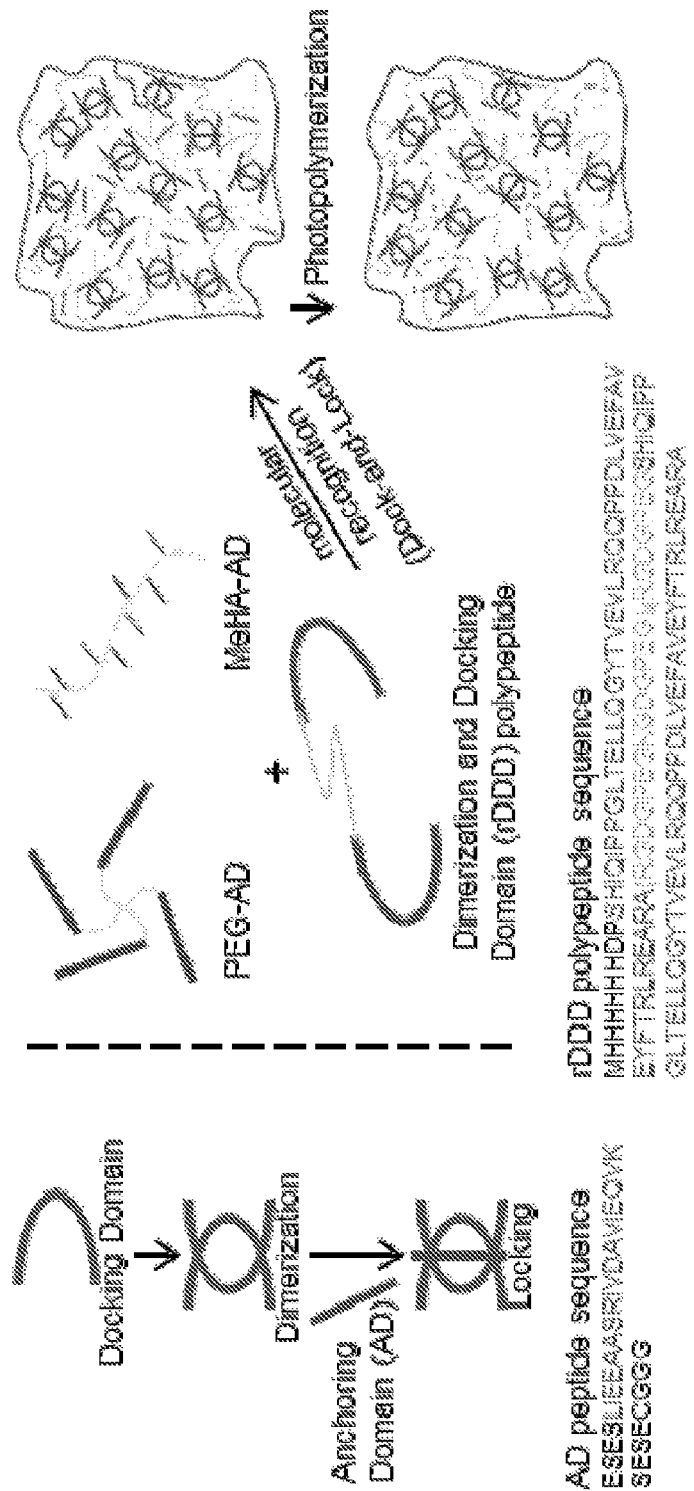
FIG. 1 provides a schematic representation illustrating the concepts associated with the Dock-and-Lock self-assembling mechanism and components described herein, including secondary radical polymerization stabilization. Recombinant docking domains dimerize and lock with the anchoring domain. Anchoring domains grafted on hyaluronic backbones assemble with docking domains to form dynamic, shear thinning, self-healing hydrogels when mixed.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to methods of operating a device and systems and to the devices and systems providing said methods. That is, where the disclosure describes and/or claims a particular hydrogel, it is appreciated that these descriptions and/or claims also describe and/or claim the methods associated with the preparation and use of such a hydrogel.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself.

The present invention(s) are directed to settable, shear-thinning hydrogels, which comprise non-covalent crosslinks (giving rise to the ability to deform and flow into liquids under shear-stress and recover back into hydrogels upon stress removal), as well as chemical moieties which provide for the ability to form chemical covalent crosslinks which can then stabilize the hydrogel network. In certain embodiments, this recovery from shear is complete within minutes or even seconds. These materials can encapsulate therapeutic cargo ex vivo in consistent and controlled conditions, and can be delivered with minimally invasive techniques via-shear-induced flow through a catheter, so as to be surgically implantable with minimal risk of premature polymerization/catheter clogging, as the settable, shear-thinning hydrogel will thin and flow while stress is applied, and can rapidly recover at the target site when stress is removed. Upon delivery, the hydrogels may be further stabilized by a secondary cross-linking, and those hydrogels with sufficient high and robust dual cross-linking functionality have the potential to support and enhance biomedical applications.

Various embodiments, then, provide settable (curable), shear-thinning hydrogels, each hydrogel comprising a hydrophilic polymer network, said hydrophilic polymer network comprising non-covalent crosslinks and at least one set of chemical moieties being capable of participating in at least one chemical covalent cross-linking reaction.

Throughout this specification, words are to be afforded their normal meaning, as would be understood by those skilled the relevant art. However, so as to avoid misunderstanding, the meanings of certain terms will be specifically defined or clarified.

As used herein, the term "hydrogel" is intended to connote that meaning normally associated with that term—i.e., a three-dimensional hydrophilic polymeric network that are hydrophilic, in which water is the dispersion medium, and are capable of maintaining their structural integrity. Hydrogels are highly swollen (they can contain over 99.9% water) natural or synthetic polymers. Hydrogels also possess a degree of flexibility very similar to natural tissue, due to their significant water content.

Similarly, in the present context, the term shear thinning has a meaning normally associated with that term—i.e., an effect where a fluid's viscosity (the measure of a fluid's resistance to flow) decreases with an increasing rate of shear stress. As contemplated herein, such shear-thinning hydrogels are composed of two or more polymers or oligomers that are held together in unique structural relationships by forces other than those of full covalent bonds. Non-covalent bonding is critical in maintaining the three-dimensional structure of the hydrogels. There are four commonly mentioned types of non-covalent interactions: hydrogen bonds, ionic bonds, van der Waals forces, and hydrophobic interactions, each of which is employed in various embodiments of the shear-thinning hydrogels contemplated herein.

As described herein, a shear-thinning hydrogel is a hydrogel capable of self-assembling into a gelled network by interaction of its associated non-covalent linkages. When subjected to a mechanical shear (such as when forced to flow through a needle, catheter, or cannula), at least some of the non-covalent linkages within the hydrogel disassociate, leading to a disassembly of the gel network and a temporary thinning of the gel (lowering of the viscosity). Upon the removal of the mechanical shear force, the original gel re-assembles/recovers to a state (e.g., viscosity, stiffness, or diffusivity) the same as, or close to, it pre-shear state. The term "shear-thinning hydrogels" are used in the literatures to describe such gels where the recovery of the hydrogel after shear can be nearly instantaneous or be as long as hours. While the present invention contemplates hydrogels which are included within this broad context, particular independent embodiments include those characterized as "rapid healing" or "rapid recovery" hydrogels, where, upon the removal of the mechanical shear force, the original gel recovers within 30 minutes, preferably within about 20, 10, 5 or about 1 minute, or within about 60, 45, 15, 10, 5, or about 1 second. The types of shear-thinning hydrogels falling within this narrower category are summarized in Guvendiren, et al., "Shear-thinning hydrogels for biomedical applications," *Soft Matter*, 2012, 8, 260-272, which is incorporated by reference herein in its entirety for all purposes. All of the hydrogels described within this Guvendiren article, modified to incorporate the chemical moieties capable of participating in at least one chemical covalent cross-linking reaction, as could be accomplished by the skilled artisan, are considered separate embodiments of the present invention.

For the sake of absolute clarity, in specific embodiments, the settable shear-thinning hydrogel comprises a peptide-based hydrogel, a protein-based hydrogel, a blended polymer hydrogel, a colloidal hydrogel, or a guest-host-based hydrogel.

In particular embodiments, each settable, shear thinning hydrogel comprises a guest-host-based hydrogel, comprising a host-polymer and a guest-polymer, linked through a plurality of host-guest pairings of non-covalent bonding moieties (plurality here refers to number of crosslinks, not necessarily types of non-covalent crosslinks). A subset of these embodiments provides that the host-polymer comprises a first hydrophilic polymer comprising a plurality of a moieties having a hydrophobic cavity; and the guest-polymer comprises a second hydrophilic polymer comprising a plurality of hydrophobic anchoring moieties (again here, plurality here refers to number of crosslinks, not necessarily types of non-covalent crosslinks). More specific embodiments provide that the moieties capable of providing a hydrophobic cavity comprise a calixarene, a cucurbit[n]uril, or a cyclodextrin, in each case optionally substituted with one or more pendant alkyl, alkanol (e.g., hydroxypropanol), alcohol, alkoxy, aromatic, sugar moieties or vinyl groups. Embodiments described as comprising an optionally substituted cyclodextrin, include those wherein the cyclodextrin is an alpha, beta, or gamma-cyclodextrin, preferably an optionally substituted beta-cyclodextrin.

Another subset of embodiments wherein the settable, shear thinning hydrogel of the present invention comprises a guest-host-based hydrogel includes those wherein the hydrophobic anchoring moiety comprises a linear, branched, cyclic, or polycyclic $C_{6-20}$ hydrocarbon, $C_{6-20}$ aryl or alkylaryl, hetero or alkylaromatic hydrocarbon moieties. In one preferred embodiment, the hydrophobic anchoring moiety comprises an adamantane.

Certain other embodiments described as involving a guest-host strategy, include those wherein the host-guest pairing of moiety comprise an alpha-cyclodextrin/hexyl group pair, an alpha-cyclodextrin/polyethylene oxide group pair, a beta-cyclodextrin/adamantane group pair, a beta-cyclodextrin/cyclohexyl group pair, a beta-cyclodextrin/benzyl group pair, a gamma-cyclodextrin/cyclodecyl group pair, a cucurbit[6]uril/hexanediamine group pair, or a cucurbit[6]uril/spermine group pair.

Within those embodiments described by a guest-host relationship, the first and second polymers associated with the host-polymer and guest-polymer, respectively, may each comprise any of the polymers described below, but preferred embodiments are those wherein at least one of the first or second hydrophilic polymers comprises hyaluronic acid. In other preferred embodiments, both the first and second hydrophilic polymers both comprise hyaluronic acid.

In a specific, non-limiting example, the host-polymer moiety comprises a polymer comprising hyaluronic acid to which is attached a plurality of a beta-cyclodextrin moieties; and the guest-polymer comprises a polymer comprising hyaluronic acid to which is attached a plurality of a adamantine groups; and the at least one set of chemical moieties capable of chemically, covalently cross-linking the hydrogel is an acrylic or methacrylate group. When the components are mixed, the hydrophobic adamantine becomes non-covalently bound inside of the hydrophobic beta-cyclodextrin cavity to yield physical cross-links and self-assembly to form a settable, shear-thinning hydrogel. Secondary covalent cross-linking of the material is obtainable by the photocatalytic, free-radical crosslinking of the acrylate groups.

In certain embodiments, the host-polymer comprises a moiety having a hydrophilic cavity linked to a first hydrophilic polymer; and the guest-polymer comprises a hydrophilic anchoring moiety linked to a second hydrophilic polymer. Such a hydrophilic cavity may comprise a cryptand or crown ether.

In other embodiments, the settable, shear thinning hydrogel of the present invention operates by a two-component Dock-and Lock (DnL) self-assembling hydrogelation mechanism, using bio-conjugate materials. Such a mechanism, and the associated class of shear thinning hydrogels, is described in H. D. Lu, M. B. Charati, I. L. Kim, J. A. Burdick, Injectable Shear-Thinning Hydrogels Engineered with a Self-Assembling Dock-and-Lock Mechanism, *Biomaterials*, 33:2145-2133, 2012, which is incorporated by reference herein for all purposes. All of the hydrogels described within this Lu article, modified to incorporate the chemical moieties capable of participating in at least one chemical covalent cross-linking reaction, as could be accomplished by the skilled artisan, are considered separate embodiments of the present invention. In certain of these embodiments, the hydrogel comprises a docking and dimerization domain (rDDD), comprising a dimer of RIM cAMP dependent PKA recombinant protein, linked together by a hydrophilic peptide spacer containing integrin binding domains. These hydrogels may also or alternatively comprise a locking anchoring domain (LOCK-AD), wherein the LOCK-AD comprises an A-kinase anchoring polypeptide modified with solubilizing amino acid sequences conjugated hydrophilic polymer backbone. These rDDD and LOCK-AD moieties may be linked by any of the hydrophilic polymers described below, but preferably comprise polyethylene glycol or hyaluronic acid. In preferred embodiments, the at least one set of chemical moieties being capable of participating in at least one chemical covalent cross-linking reaction in these DnL hydrogels comprise an acrylate or methacrylate group at the peptide N terminus or along the hydrophilic polymer backbone, said acrylate or methacrylate group capable of polymerizing with exposure to light.

These polymeric DnL conjugated materials can undergo triggered self-assembly via a molecular recognition based 'Dock-and-Lock' mechanism under constant physiological conditions (strategy illustrated in FIG. 1). In particular embodiments, these settable, shear thinning hydrogels can be 'stabilized' by the radical polymerization of reactive methacrylates that are also included on the polymer.

As described above, various embodiments, provide settable (curable), shear-thinning hydrogels, each hydrogel comprising a hydrophilic polymer network, said hydrophilic polymer network comprising non-covalent crosslinks and at least one set of chemical moieties being capable of participating in at least one chemical covalent cross-linking reaction. In certain embodiments, the "at least one set of chemical moieties being capable of participating in at least one chemical covalent cross-linking reaction" are operable (or begin to chemical crosslink) spontaneously upon formation (mixing) of the shear-thinning hydrogel. The types of chemical moieties which may accomplish this "spontaneous" covalent crosslinking may be described in terms of the chemistries described below, but preferred embodiments are those where the reactants are chosen such that the kinetics of the covalent cross-linking are "slow" with respect to mixing and application to the intended site. That is, the term "slow" reflects that the chemical covalent crosslinking provides an observable effect on the properties of the gel only at times in excess of 30 minutes. In but one example, systems comprising a hydrophilic polymer modified with vinyl sulfone and another modified with a thiol may be used.

In comparison, separate embodiments provide those settable (curable), shear-thinning hydrogels, wherein the at least one chemical covalent cross-linking reaction is initiated by an internal or external (both relative to the hydrogel itself) trigger. In these embodiments, the shear-thinning hydrogels may be described as "selective settable" hydrogels, the term "selective" referring to the fact that the user may select when and how to initiate the chemical covalent cross-linking reactions (beyond the act simple mixing).

The hydrophilic polymer network of the settable shear thinning hydrogels may also comprise more than one—i.e., at least two—sets of chemical moieties, each set being capable of independently participating in at least one chemical covalent cross-linking reaction. That is, in various aspects of the present invention, a given hydrogel may contain one, two, or more sets of chemical moieties capable of participating in a chemical covalent crosslinking reaction. In separate embodiments, these occur spontaneously or as triggered. Each covalent cross-linking reaction may occur by a similar mechanism (e.g., a condensation reaction), albeit with different chemical moieties, or by different mechanisms. In either case the reactions may be independently triggered (e.g., by different wavelengths of light or application of different stimuli), by an internal or external stimulus or stimuli, or operate at different rates (e.g., two condensation reactions may have different kinetics by virtue of different nucleophiles, electrophiles, steric hindrance, etc.).

Figure 10A:
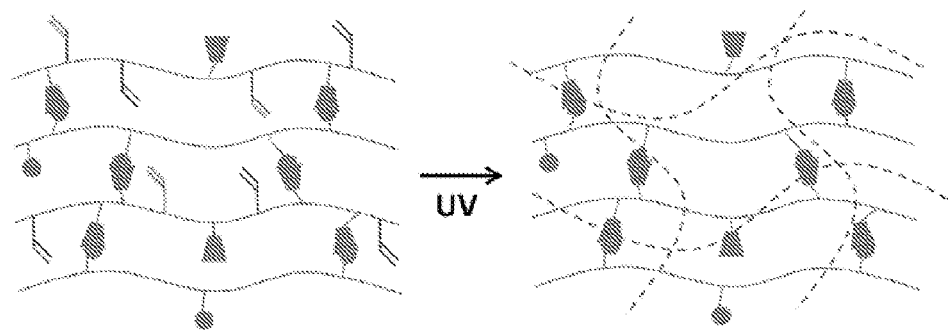
FIG. 10 is shown to contrast the system of FIG. 9 where the chemical cross-linking of the methacrylate vinyl groups upon photopolymerization stabilized the hydrogel network. Hydrogels were formed by mixing of Ad-HA and CD-MeHA components at 7.5 wt % where CD and Ad functionality are in a 1:1 ratio. The solvent used for preparation was PBS containing 4-(2-hydroxyethoxyl)phenyl-(2-hydroxy-2-propyl)ketone (Irgacure 2959, 12959) at 0.05 wt % as a radical initiator Throughout photopolymerization (initiated with ultraviolet light, 365 nm, 150 µW/cm$^2$), an increase in moduli was observed and shear-thinning behavior subsequently found to be arrested. A frequency sweep confirmed the secondary covalent cross-linking results in a solid hydrogel. The moduli plateau at low frequency where the storage modulus is greater than the loss modulus for all frequencies observed, confirming the network is no longer capable of dynamic flow.
Figure 10B:
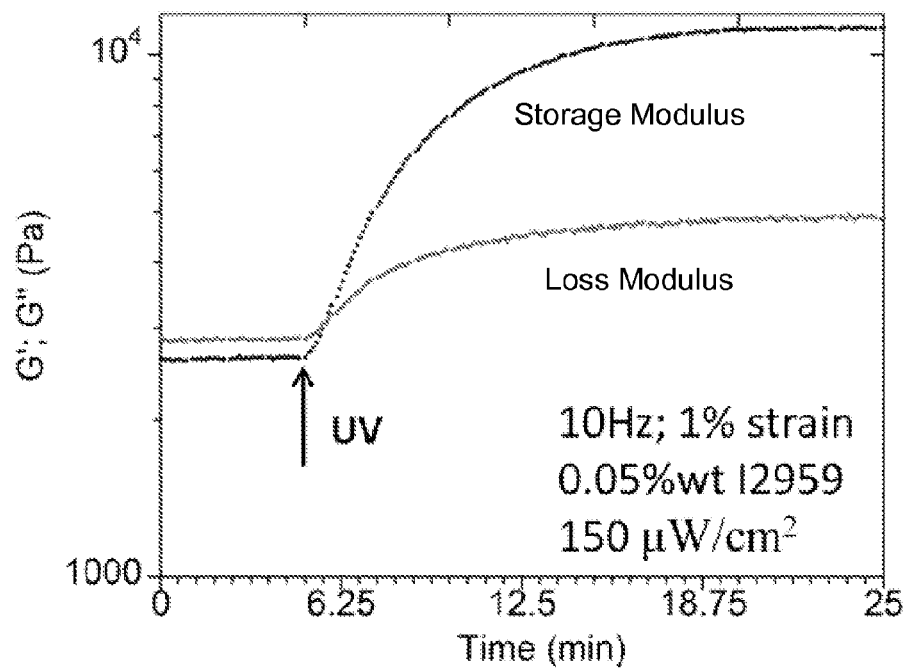

For each mechanism, the chemical covalent crosslinking results in a covalently cross-linked hydrogel having a mechanical stability that is higher than the mechanical stability of the shear-thinning hydrogel before chemical cross-linking. In separate embodiments, this "higher" mechanical stability may be described in terms of improved resistance to bio-erosion—defined in terms of disassociation of the non-covalent linkages; i.e., improved resistance correlating with longer times necessary to realize degradation of the polymer network—or increased viscosity, stiffness or higher storage or loss modulus of the polymer network. Within each of these property classes, this higher stability reflects an improvement or increase in at least one physical property of at least about 10%, at least about 25%, at least about 50%, or at least about 100%, or at least about 2 times, at least about 5 times, or at least about 10 times relative to the corresponding property of the shear-thinning hydrogel. So as to be clear, in one exemplary embodiment, FIG. 7 shows that a cross-linked DnL gel remains stable (i.e., at a normalized erosion of ca. 10%) for more than 8 weeks, whereas the non-cross-linked hydrogel is virtually completely degraded within days. In another example, FIG. 10 illustrates that the storage modulus of a modified cyclodextrin/adamantine/hyaluronic acid hydrogel network increased from ca. 2000 to more than about 10,000 Pa after crosslinking the pendant methacrylate groups.

In other embodiments, the chemical covalent crosslinking moieties are capable of, or actually, resulting in a covalently cross-linked hydrogel having a mechanical stability that is higher than the mechanical stability of the shear-thinning hydrogel before chemical cross-linking and/or the chemical covalent crosslinking reaction provides a covalently cross-linked hydrogel exhibiting reduced diffusivity of an entrained material relative to the diffusivity exhibited by the shear-thinning hydrogel before chemical cross-linking. As contemplated herein, the entrained material may include a pharmaceutically active drug or neutraceutical, a population of cells, a nanoparticle, quantum dot, or magnetic material. The diffusivity rate would be measured by standards means, for example by measuring the release of a macromolecule of known molecular weight (e.g., a dextran or bovine serum albumin) form a hydrogel into solution or by measuring the uptake of the same molecules into the hydrogel.

As described above, the settable, shear-thinning hydrogels comprise a hydrophilic polymer network, comprising hydrophilic polymers or copolymers containing hydrophilic polymer subunits. These polymers may comprise natural, synthetic, biocompatible, biodegradable, non-biodegradable, and/or biosorbable building blocks. Unless specifically restricted to one or more of these categories, the polymers may comprise materials from any one of these categories. For performance reasons, it may be desirable to incorporate biodegradable or porogenic materials into the design.

The term "polymer" is not intended to necessarily refer to a single polymer molecule; rather it is intended to connote a mixture of individual molecules, said mixture having a distribution of molecular weights, as is understood by those skilled in the art. The present invention is not limited to any particular molecule weight distribution, provided the distribution provides a mixture suitable for the purposes described herein. For example, a polymer comprising hyaluronic acid refers to a mixture of individual polymer molecules, each molecule comprising hyaluronic acid.

The phrase "synthetic polymer" refers to polymers that are not found in nature, even if the polymers are made from naturally occurring biomaterials. Examples include, but are not limited to, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polysiloxanes, and combinations thereof.

Suitable synthetic polymers for use according to the teachings of the present invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include collagen-based materials, chitosan, hyaluronic acid and alginate.

The phrase "biocompatible polymer" refers to any polymer (synthetic or natural) which when in contact with cells, tissues or body or physiological fluid of an organism does not induce adverse effects such as immunological reactions and/or rejections and the like. It will be appreciated that a biocompatible polymer can also be a biodegradable polymer.

The phrase "biodegradable polymer" refers to a synthetic or natural polymer which can be degraded (i.e., broken down) in the physiological environment such as by enzymes, microbes, or proteins. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. Aliphatic polyesters, poly(amino acids), polyalkylene oxalates, polyamides, polyamido esters, poly(anhydrides), poly(beta-amino esters), polycarbonates, polyethers, polyorthoesters, polyphosphazenes, and combinations thereof are considered biodegradable. More specific examples of biodegradable polymers include, but are not limited to, collagen (e.g., Collagen I or IV), fibrin, hyaluronic acid, polylactic acid (PLA), polyglycolic acid (PGA), polycaprolactone (PCL), poly(Lactide-co-Glycolide) (PLGA), polydioxanone (PDO), trimethylene carbonate (TMC), polyethylene glycol (PEG), Collagen, PEG-DMA, alginate or alginic acid, chitosan polymers, or copolymers or mixtures thereof.

The phrase "non-biodegradable polymer" refers to a synthetic or natural polymer which is not degraded (i.e., broken down) in the physiological environment. Examples of non-biodegradable polymers include, but are not limited to, carbon, nylon, silicon, silk, polyurethanes, polycarbonates, polyacrylonitriles, polyanilines, polyvinyl carbazoles, polyvinyl chlorides, polyvinyl fluorides, polyvinyl imidazoles, polyvinyl alcohols, polystyrenes and poly(vinyl phenols), aliphatic polyesters, polyacrylates, polymethacrylates, acyl-substituted cellulose acetates, non-biodegradable polyurethanes, polystyrenes, chlorosulphonated polyolefins, polyethylene oxides, polytetrafluoroethylenes, polydialkylsiloxanes, and shape-memory materials such as poly (styrene-block-butadiene), copolymers or mixtures thereof.

The phrase "biosorbable" refers to those polymers which are absorbed within the host body, either through a biodegradation process, or by simple dissolution in aqueous or other body fluids. Water soluble polymers, such as poly (ethylene oxide) are included in this class of polymers.

The term "co-polymer" as used herein, refers to a polymer of at least two chemically distinct monomers. Non-limiting examples of co-polymers which may be used within the hydrogels of the present invention include, PLA-PEG, PEGT-PBT, PLA-PGA, PEG-PCL and PCL-PLA. The use of copolymers or mixtures of polymers/copolymers provides a flexible means of providing the required blend of properties. In but one non-limiting example, functionalized poly (β-amino esters), which may be formed by the conjugate addition of primary or secondary amines with di-acrylates, can provide a range of materials exhibiting a wide array of advantageous properties for this purpose. Such materials are described, for example, in Anderson, et al., "A Combinatorial Library of Photocrosslinkable and Degradable Materials," Adv. Materials, vol. 18 (19), 2006, this reference being incorporated by reference in its entirety.

In certain preferred embodiments, the settable shear-thinning hydrogels comprise an agarose, alginate, RGD-modified alginate, amylase, amylpectin, cellularose, chitosan, collagen, dextran, fibrin, gelatin, glycogen, heparin, hyaluronic acid, oligo(poly(ethylene glycol)fumarate), poly (ε-caprolactone), poly(ethylene glycol), poly(acrylamide), poly(β-aminoester), poly(caprolactone), multi-arm polyethylene glycol, poly-hydroxyethyl acrylate, poly(hydroxyethyl methacrylate), poly(N-isopropylacrylamide), poly (glycolic acid), poly(lactic acid), poly(lactic acid-glycolic acid), oligo(poly(ethylene glycol)fumarate), poly(vinyl alcohol), or a poly(vinyl acid).

With the respect to the chemical moieties capable of chemical covalent crosslinking, the term "at least one set" refers to the fact that typically, but not necessarily, are the chemical moieties are different chemical groups which react together to form a cross-link; i.e., from this perspective, the "at least one set" may be envisioned as comprising a matched pair of chemical groups. For example, a set may comprise a carboxylic acid (or equivalent) and an amine or alcohol (or equivalent), together capable of forming an amide or ester cross-linked linkage. In another example, a set may comprise a thiol group and a vinyl group, together capable of forming a thiol ether on reaction with light. Another set may comprise a hydrazide and an aldehyde or ketone, capable of forming a hydrazone. Or a set may comprise simply a single radical polymerizable moiety, such as an acrylate or methacrylate.

In individual embodiments, each of the different chemical groups which may react together to form a covalent cross-link within the network may be attached to the same or a different polymer within the polymer network. In non-limiting examples relating to the guest-host-based hydrogels described above, for a given set of chemical cross-linkable moieties, (a) one chemical group may be attached to the first polymer while the associated "matching" chemical group is attached to the second polymer, or (b) both chemical groups may be attached to either the first or second polymer' or (c) a combination of the (a) and (b). Where more than one set of chemical covalent cross-linkable moieties are present, each set may be independently arranged are described above.

These at least one set of chemical covalent cross-linkable moieties may be attached as a pendant to at least one polymer of the network, either directly to the polymer backbone or via a linking group. In some embodiments, this linking group may be biodegradable (e.g., under physiological conditions), such that after the hydrogel is cross-linked, the linking group may degrade with time, thereby reducing the physical strength of the original cross-linked performance or releasing any cargo contained within the cross-linked hydrogel.

In other embodiments, the chemical covalent cross-linkable moieties may be embedded within the polymer backbone of at least one polymer of the network. Olefin or epoxy moieties may be examples of this strategy.

In other embodiments, the settable, shear thinning hydrogel may comprise moieties capable of fluorescing or phosphorescing after exposure to light. Such moieties are known in the art, for example a Cy7.5 dye. Such a marker would be useful, for example, to measure degradation (or stability) performance of the hydrogel in use, or trigger-able upon exposure to a specific analyte in a sensor application.

In certain embodiments, where the chemical moieties capable of chemical covalent crosslinking are activated, or "triggered" by exposure to radiation, for example light of a specific wavelength or wavelengths (i.e., the hydrogel may contain multiple such chemical sets, each triggerable by a different wavelength of light). In such case, the stimulus/stimuli may be light having a wavelength within the near infrared to ultraviolet range. See, e.g., Tan, et al., *J. Biomed Mad. Res.*, vol. 87 (4), 2008, pp. 1034-1043, which is incorporated by reference in its entirety, for examples of chemical moieties triggerable by light. In those compositions wherein the chemical moieties are light activated, it would also be advantageous that the hydrogel further comprises a photo-initiator; for example, 1-[4-(2-hydroxy-ethoxy)-phenyl]-2-hydroxy-2-methyl-1-propane-1-one, available from Ciba Specialty Chemicals, Inc. as IRGACURE 2959. Other exemplary photo-initiators include 2,4,6 trimethylbenzoyldiphenyl phosphine oxide, 2-hydroxy-2-methyl-1-phenyl-propanone, oligo (2-hydroxy-2-methyl-1-(4-(1-methylvinyl)vinyl) propanone), and 2,4,6-trimethyl-benzophonone.

In other embodiments, the external stimulus to the chemical covalent crosslinking reaction may be radiation in the microwave range (i.e., in the range of about 1 MHz to about 10 GHz). In still other embodiments, the external stimulus may be a change in pH or temperature, a free radical initiator, or a combination thereof. Where the chemical covalent cross-linking reaction is a free radical polymerization, the hydrogel may further comprise a thermal radical initiator. Exemplary free radical initiators include azobisisobutyronitrile, dilauroyl peroxide lauroyl acid, dioctanoyl peroxide caprylic acid, didecanoyl peroxide n-decanoic acid, di-n-propionyl peroxide propionic acid, bis(3,5,5-trim-ethyl hexanoyl) 3,5,5-trimethyl peroxide hexanoic acid, dibenzoyl peroxide benzoic acid, bis(2,4-dichlorobenzoyl) 2,4 dichlorobenzoic acid peroxide, bis(o-methybenzoyl) peroxide o-methyl benzoic acid, acetyl cyclohexane sulphonyl cyclohexane sulphonic peroxide acid, t-butylperoxypivalate pivalic acid, t-butyl peroxy-2-ethylhexanoate 2-ethyl caproic acid, t-butyl peroxy isobutyrate isobutyric acid, t-butyl peroxybenzoate benzoic acid, and mixtures thereof.

In certain embodiments, the covalent crosslinking reaction is a condensation reaction, Michael addition, or a free radical polymerization reaction. In related embodiments, the at least one set of chemical moieties capable of participating in a covalent chemical crosslinking reaction comprises an acrylate, acrylamide, optionally protected alcohol, aldehyde, alkyne, optionally protected amine, anhydride, azide, carboxy, epoxy, ester, hydrazide, ketone, maleimide, methacrylate, styrenyl, optionally protected thiol, or vinyl or vinyl sulfone group. In still further related embodiments, the product of the chemical covalent cross-linking reaction is an ester, ether, amide, hydrozone, polyacrylate, polymethacrylate, thioamide, thioester, thioether, or urethane. This skilled artisan would appreciate how to modify the desired polymer to attached or incorporate, the chemical covalent cross-linkable moiety.

Other embodiments describe these additional materials as comprising biofactors, therapeutic agents, particles (e.g., nanoparticles, quantum dots, or magnetic materials), or cells.

In one set of embodiments, these additional materials comprise at least one therapeutic compound or agent, capable of modifying cellular activity. Similarly, agents that act to increase cell attachment, cell spreading, cell proliferation, cell differentiation and/or cell migration in the scaffold may also be incorporated into the hydrogels. Such agents can be biological agents such as an amino acid, peptides, polypeptides, proteins, DNA, RNA, lipids and/or proteoglycans. These agents may also include growth factors, cytokines, proteases, and protease substrates.

Additionally and/or alternatively, the settable hydrogels of the present invention may comprise an antiproliferative agent, an immunosuppressant drug, and/or a non-thrombogenic or anti-adhesive substance.

The cells which can be used according to the teachings of the present invention may comprise non-autologous cells or non-autologous cells (e.g. allogeneic cells or xenogeneic cells), such as from human cadavers, human donors or xenogeneic (e.g. porcine or bovine) donors.

The cells may comprise a heterogeneous population of cells or a homogeneous population of cells. Such cells can be for example, stem cells, progenitor cells, or differentiated cells. Stem cells may include adipose derived stem cells, embryonic stem cells, bone marrow stem cells, cord blood stem cells, mesenchymal stem cells, adult stem cells, and pluripotent or induced pluripotent stem cells. Mesenchymal stem cells are preferred.

Furthermore, such cells may be live or non-viable and/or of autologous origin or non-autologous origin, such as postpartum-derived cells (as described in U.S. application Ser. Nos. 10/887,012 and 10/887,446). Typically the cells are selected according to the tissue being generated.

In additional to the settable, shear thinning hydrogels (i.e., which exists before the covalent crosslinking reaction(s) has occurred or is complete), individual embodiments of the present invention include those hydrogel compositions, based on the previous descriptions, which have undergone at least one of the covalent cross-linking reactions, either partially or completely. This includes embodiments where any number of the at least one set of the chemical moieties capable of covalent crosslinking of settable, shear thinning hydrogel has reacted, either partially or entirely.

In separate embodiments, the cured hydrogels exhibit a higher stability or lower diffusivity than the pre-cured (i.e., settable, shear thinning) hydrogel. In several of these embodiments, the cured, covalently cross-linked hydrogel exhibits a mechanical stability that is higher than the mechanical stability of the (pre-cured) shear-thinning hydrogel (i.e., before covalent crosslinking). In separate embodiments, this "higher" mechanical stability may be described in terms of improved resistance to bio-erosion—defined in terms of disassociation of the non-covalent linkages; i.e., improved resistance correlating with longer times necessary to realize degradation of the polymer network—or increased viscosity, stiffness or higher storage or loss modulus of the polymer network. Within each of these property classes, this higher stability reflects an improvement or increase in at least one physical property of at least about 10%, at least about 25%, at least about 50%, or at least about 100%, or at least about 2 times, at least about 5 times, or at least about 10 times, relative to the corresponding property of the shear-thinning hydrogel. So as to be clear, in one exemplary embodiment, FIG. 7 shows that a cross-linked DnL gel remains stable for more than 8 weeks (normalized erosion ca. 10%), whereas the non-cross-linked cogener is virtually completely degraded within days. In another example, FIG. 10 illustrates that the storage modulus of a modified cyclodextrin/adamantine/hyaluronic acid hydrogel network increased from ca. 2000 to more than about 10,000 Pa after crosslinking the pendant methacrylate groups.

Further, the settable, shear-thinning hydrogels and associated cured hydrogels may be applied in-vivo and/or ex-vivo. Various embodiments provide that the settable or cured hydrogels are adapted to be medically acceptable for use in a mammal, including those where the mammal is a human. Such embodiments include those where the materials are at least biocompatible, and preferably approved by the United States Food and Drug Administration in the United States (or a corresponding regulatory agency in other countries).

The materials described herein may be used to controls encapsulated cell behavior, improve delivered cell retention, and control cellular release rates. These materials can also be used to tune encapsulated drug release profiles and pharmokinetics.

Additional exemplary applications of the present invention include those where the settable, shear-thinning hydrogels and associated cured hydrogels:
scaffolds in tissue engineering;
vehicles for cell encapsulation and delivery;
sustained- or controlled release drug delivery systems;
biosensors, including those responsive to specific molecules, such as glucose or antigens;
contact lenses;
adhesives, including medical and electronic adhesives
biosealants;
dressings for healing of burn or other hard-to-heal wounds.
and reservoirs in topical drug delivery; particularly ionic drugs, delivered by iontophoresis Certain embodiments also provide methods of preparing a controlled or sustained release formulation of a pharmaceutically active drug, neutraceutical, cell population, or particle array in a patient, each method comprising introducing into the patient a composition comprising a settable, shear-thinning hydrogel as described herein, and a pharmaceutically active drug, neutraceutical, cell population; or particle. Other embodiments further comprise triggering at least one chemical covalent crosslinking reaction.

Other independent embodiments provide methods of preparing a controlled release formulation of a pharmaceutically active drug, neutraceutical, or cell population in a patient, each method comprising introducing into a patient the composition comprising (a) a settable shear-thinning hydrogel comprising a network hydrophilic polymers, said hydrophilic polymer network comprising non-covalent crosslinks and at least one set of chemical moieties being capable of participating in at least one chemical covalent cross-linking reaction; and (b) a pharmaceutically active drug, neutraceutical, or cell population. Other embodiments further comprise triggering at least one chemical covalent crosslinking reaction.

Among the many embodiments considered within the scope of the present invention are these:

Embodiment 1. A [selectively] settable, shear-thinning hydrogel comprising a hydrophilic polymer network, said hydrophilic polymer network comprising non-covalent crosslinks and at least one set of chemical moieties being capable of participating in at least one chemical covalent cross-linking reaction.

Embodiment 2. The hydrogel of Embodiment 1, wherein the hydrophilic polymer network comprise at least two sets of chemical moieties, each set being capable of independently participating in at least one chemical covalent cross-linking reaction.

Embodiment 3. The hydrogel of Embodiment 1 or 2, wherein at least one set of chemical moieties is capable of participating in a chemical covalent cross-linking reaction within the hydrogel when triggered by an external stimulus.

Embodiment 4. The hydrogel of any one of the preceding Embodiments, wherein the chemical covalent crosslinking reaction provides a covalently cross-linked hydrogel having a mechanical stability that is higher than the mechanical stability of the shear-thinning hydrogel before chemical cross-linking.

Embodiment 5. The hydrogel of any one of the preceding Embodiments, wherein the chemical covalent crosslinking reaction provides a covalently cross-linked hydrogel exhibiting reduced diffusivity of a solute relative to the diffusivity exhibited by the shear-thinning hydrogel before chemical cross-linking.

Embodiment 6. The hydrogel of any one of the preceding Embodiments, wherein the shear-thinning hydrogel comprises a peptide-based hydrogel, a protein-based hydrogel, a blended polymer hydrogel, a colloidal hydrogel, or a guest-host-based hydrogel.

Embodiment 7. The hydrogel of any one of the preceding Embodiments, wherein the hydrophilic polymer network comprises an agarose, alginate, RGD-modified alginate, amylase, amylpectin, cellularose, chitosan, collagen, dextran, fibrin, gelatin, glycogen, heparin, hyaluronic acid, poly(acrylamide), poly(β-aminoester), poly(caprolactone), matrigel, multi-arm polyethylene glycol, poly-hydroxyethyl acrylate, poly(hydroxyethyl methacrylate), poly(N-isopropylacrylamide), poly(glycolic acid), poly(lactic acid), poly(lactic acid-glycolic acid), oligo(poly(ethylene glycol)fumarate), poly(vinyl alcohol), or a poly(vinyl acid).

Embodiment 8. The hydrogel of any one of the preceding Embodiments, wherein the at least one set of chemical moieties capable of crosslinking is pendant to at least one polymer of the network.

Embodiment 9. The hydrogel of Embodiment 8, wherein at least one of the chemical moieties capable of covalent crosslinking is attached to a polymer within the network by a linking group.

Embodiment 10. The hydrogel of Embodiment 9, wherein the linking group is biodegradable under physiological conditions.

Embodiment 11. The hydrogel of any one of the preceding Embodiments, further comprising a moiety capable of fluorescing or phosphorescing after exposure to light.

Embodiment 12. The hydrogel of any one of the preceding Embodiments, wherein at least one set of chemical moieties capable of covalent crosslinking is incorporated within at least one polymer of the network.

Embodiment 13. The hydrogel of any one of Embodiments 3-12, wherein the external stimulus is light.

Embodiment 14. The hydrogel of Embodiment 13, further comprising a photo-initiator.

Embodiment 15. The hydrogel of any one of Embodiments 3-12, wherein the external stimulus is microwave radiation.

Embodiment 16. The hydrogel of any of any one of Embodiments 3-12, wherein the external stimulus is a change in pH or temperature, a free radical initiator, or a combination thereof.

Embodiment 17. The hydrogel of Embodiment 16, further comprising a thermal radical initiator.

Embodiment 18. The hydrogel of any one of the preceding Embodiments, wherein the covalent crosslinking reaction is a condensation reaction, Michael addition, or a free radical polymerization reaction.

Embodiment 19. The hydrogel of any one of the preceding Embodiments, wherein at least one set of chemical moieties capable of participating in a covalent chemical crosslinking reaction comprises an acrylate, acrylamide, optionally protected alcohol, aldehyde, alkyne, optionally protected amine, anhydride, azide, carboxy, epoxy, ester, hydrazide, ketone, maleimide, methacrylate, styrenyl, optionally protected thiol, or vinyl or vinyl sulfone group.

Embodiment 20. The hydrogel of any one of the preceding Embodiments, wherein a product of the chemical covalent cross-linking reaction is an ester, ether, amide, hydrozone, polyacrylate, polymethacrylate, thioamide, thioester, thioether, or urethane Embodiment 21. The hydrogel of any one of the preceding Embodiments, wherein the shear-thinning hydrogel comprises a guest-host-based hydrogel, comprising a host-polymer and a guest-polymer, linked through a plurality of host-guest pairings of moieties.

Embodiment 22. The hydrogel of Embodiment 21, wherein the host-polymer comprises a first hydrophilic polymer comprising a plurality of moieties each having a hydrophobic cavity; and the guest-polymer comprising a second hydrophilic polymer comprising a plurality of hydrophobic anchoring moieties.

Embodiment 23. The hydrogel of Embodiment 22, wherein the moiety capable of providing a hydrophobic cavity comprises a calixarene, a cucurbit[n]uril, or a cyclodextrin.

Embodiment 24. The hydrogel of Embodiment 22, wherein the moiety capable of providing a hydrophobic cavity comprises an optionally substituted cyclodextrin, preferably a β-cyclodextrin.

Embodiment 25. The hydrogel of any one of Embodiments 22 to 24, wherein the hydrophobic anchoring moiety comprises a linear, branched, cyclic, or polycyclic $C_{6-20}$ hydrocarbon, $C_{6-20}$ aryl or alkylaryl, hetero or alkylaromatic hydrocarbon moieties.

Embodiment 26. The hydrogel of Embodiment 21, wherein the hydrophobic anchoring moiety is an adamantane.

Embodiment 27. The hydrogel of any one of Embodiments 22 to 26, wherein the host-guest pairing of moieties comprises an alpha-cyclodextrin/hexyl group pair, an alpha-cyclodextrin/polyethylene oxide group pair, a beta-cyclodextrin/adamantane group pair, a beta-cyclodextrin/cyclohexyl group pair, a beta-cyclodextrin/benzyl group pair, a gamma-cyclodextrin/cyclodecyl group pair, a cucurbit[6]uril/hexanediamine group pair, or a cucurbit[6]uril/spermine group pair.

Embodiment 28. The hydrogel of any one of Embodiments 22 to 27, wherein at least one of the first or second hydrophilic polymers comprises hyaluronic acid.

Embodiment 29. The hydrogel of Embodiment 28, wherein the first and second hydrophilic polymers both comprise hyaluronic acid.

Embodiment 30. The hydrogel of any one of Embodiments 22 to 29, wherein the first and second hydrophilic polymers comprises at least two sets of chemical moieties, each capable of independently crosslinking the hydrogel when subjected to a separate external stimulus.

Embodiment 31. The hydrogel of Embodiment 21, wherein the host-polymer comprises a first hydrophilic polymer comprising a plurality of moieties linked thereto, each having a hydrophilic cavity; and the guest-polymer comprises a second hydrophilic polymer having a plurality of hydrophilic anchoring moieties linked thereto.

Embodiment 32. The hydrogel of Embodiment 31, wherein the moiety capable of providing a hydrophilic cavity comprises a cryptand or crown ether.

Embodiment 33. The hydrogel of any one of Embodiments 1 to 20, wherein the shear-thinning hydrogel comprises a peptide-based hydrogel.

Embodiment 34. The hydrogel of Embodiment 33, which operates by a two-component Dock-and Lock (DnL) self-assembling hydrogelation mechanism.

Embodiment 35. The hydrogel of Embodiment 33 or 34, comprising a docking and dimerization domain (rDDD), comprising a dimer of RIIa cAMP dependent PKA recombinant protein, links together by a hydrophilic peptide spacer containing integrin binding domains.

Embodiment 36. The hydrogel of Embodiment 33, comprising a locking anchoring domain (LOCK-AD), wherein the LOCK-AD comprises an A-kinase anchoring polypeptide modified with solubilizing amino acid sequences conjugated hydrophilic polymer backbone.

Embodiment 37. The hydrogel of Embodiment 36, further comprising an acrylate or methacrylate group at the peptide N terminus or along the hydrophilic polymer backbone, said acrylate or methacrylate group capable of polymerizing with exposure to light.

Embodiment 38. A cured hydrogel, where the hydrogel of any one of Embodiments 1 to 37 has been cross-linked by the reaction of the at least one set of the chemical moieties.

Embodiment 39. The cured (cross-linked) hydrogel of Embodiment 38, wherein the stability of the cross-linked hydrogel is at least 50% greater than the stability of the hydrogel before said crosslinking, when tested under comparable [physiological] conditions.

Embodiment 40. The cured (cross-linked) hydrogel of Embodiments 38 or 39, further comprising a pharmaceutically active drug or neutraceutical, a population of cells, nanoparticle, quantum dot, magnetic material, or combination thereof.

Embodiment 41. The hydrogel of Embodiment 40, wherein the diffusivity of the pharmaceutically active drug or neutraceutical, a population of cells, nanoparticle, quantum dot, or magnetic material from the cross-linked hydrogel is less than 50% greater than the stability of the hydrogel before said crosslinking, when tested under comparable [physiological] conditions.

Embodiment 42 The hydrogel of any one of Embodiments 1 to 41, wherein the hydrogel is adapted to be medically acceptable for use in a mammal.

Embodiment 43. The hydrogel of Embodiment 42, where the mammal is human.

Embodiment 44. A method of preparing a controlled or sustained release formulation of a pharmaceutically active drug, neutraceutical, or cell population in a patient, said method comprising introducing into the patient a composition comprising a hydrogel of any one of Embodiments 1 to 43 and a pharmaceutically active drug, neutraceutical, or cell population.

Embodiment 45. The method of Embodiment 44, further comprising triggering at least one chemical crosslinking reaction.

Embodiment 46. A method of preparing a controlled or sustained release formulation of a pharmaceutically active drug, neutraceutical, or cell population in a patient, said method comprising introducing into a patient the composition comprising:

(a) a settable shear-thinning hydrogel comprising a network hydrophilic polymers, said hydrophilic polymers comprising non-covalent linkages, and further comprising at least one set of chemical moieties being capable of participating in at least one chemical covalent cross-linking reaction; and (b) a pharmaceutically active drug, neutraceutical, or cell population.

Embodiment 47. The method of Embodiment 46, further comprising triggering at least one chemical covalent cross-linking reaction.

Embodiment 48. The method of Embodiment 46 or 47, wherein the hydrogel is a hydrogel of any one of Embodiments 1 to 37.

Embodiment 49. The method of any one of Embodiments 46 to 48, wherein the hydrogel is introduced into a patient by way of a needle, catheter, or cannula.

EXAMPLES

Example 1

Experimental—Poly-AD Hydrogels

Poly-AD synthesis. AD peptide was synthesized on 2-chlorotrityl chloride functionalized resin (Novabiochem) with an automated solid phase peptide synthesizer (PS3, Protein Technologies) using standard Fmoc chemistry. Sodium hyaluronate (HA; 64 kDa, LifeCore Biomedical) was converted to tetrabutylammonium hyaluronate (HA-TBA) by ion exchange over Dowex-100 resin and neutralization with tetrabutylammonium hydroxide in DI $H_2O$. HA-TBA was reacted with 2-aminoethylmaleimide trifluoroacetate salt and (Benzotriazol-1-yloxy)tris(dimethylamino)phosphonium hexafluorophosphate in DMSO, and thoroughly dialyzed with deionized $H_2O$ at 4° C. to yield maleimide functionalized hyaluronic acid (Ma-HA). AD was conjugated to maleimide end-functionalized multi-arm arm PEG (10 kDa 4armPEG/20 kDa 8arm PEG, Jenkem Technology USA) and Ma-HA via Michael-type addition between peptide cysteine and PEG maleimide reactive groups in pH 7.0 aqueous buffer, and dialyzed with DI $H_2O$ to yield 4aPEG-AD (0.76 peptides/arm), 8aPEG-AD (0.81 peptides/arm), and HA-AD (68 peptides/chain). Similar chemistry was used to synthesize MeHA-AD. Cy5.5 dye was conjugated to primary amines on Poly-AD by reaction with Cy5.5 NHS ester (Lumiprobe). ESI MS, MALDI-TOF MS, and $^1H$ NMR were used to assess and characterize Poly-AD component composition and modification.

rDDD expression and purification. DNA coding a recombinant docking and dimerization domain (rDDD) was cloned in pJExpress411 and transformed into BL21DE3*E. Coli. Protein expression in log-phase culture was initiated via the Studier auto-induction method, and purified with standard IMAC (HisTrap, GE Healthcare) procedures in denaturing conditions. See, e.g., F. W. Studier, Protein expression and purification 2005, 41, 207, which is incorporated by reference in its entirety for its teachings. Protein was refolded on IMAC columns through three volumes of chaotropic agent free buffer. MALDI-TOF MS and SDS-PAGE were used to characterize rDDD identity and purity (>95% pure).

DnL hydrogel characterization. DnL components were separately dissolved in PBS of the appropriate pH. To initiate gelation by DnL self-assembly, separate components were mixed together to appropriate compositions. Dynamic oscillatory time, frequency and strain sweeps were performed on materials using cone and plate rheometry (AR2000, Texas Instruments) to study DnL gel rheology. Moduli, relaxation time, strain yield, and strain recovery profiles as a function of gel pH, AD molecular valency, component concentrations/ratios, polymer backbone, and additional 'locking' were investigated on gels formed in PBS. Photopolymerization 'stabilization' cross-linking was initiated by UV radiation using IRGACURE™ 12959 photo-initiator. The material stability was characterized by determining gel erosion and encapsulated cargo release rates in PBS via UV-Vis spectroscopy and sandwich ELISA. The viability of mesenchymal stem cells (MSC) encapsulated and delivered with DnL gels through a 21 gauge needle were studied using confocal microscopy and Live/Dead assay.

Results and Discussion

Figure 2:
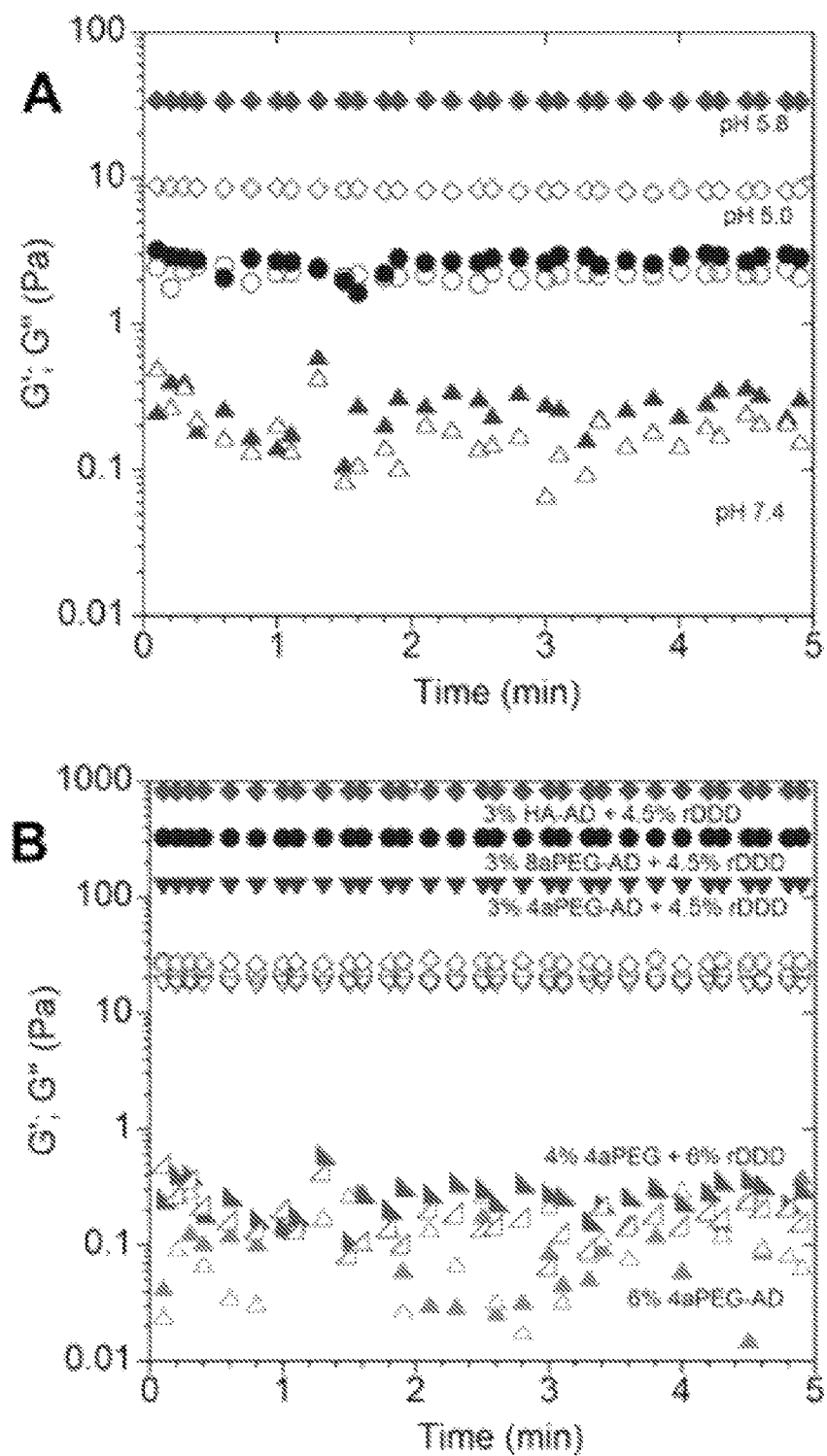
FIG. 2 provides the results of dynamic oscillatory time sweeps of 6 wt % 4aPEG-AD at various pH (storage modulus, G', filled shapes; loss modulus, G", empty shapes of DnL components alone and together at 1% strain and 6.3 rad $s^{-1}$) (FIG. 2A); and time sweeps of Poly-AD:rDDD materials at various wt % compositions (FIG. 2B). Experiments were performed under 6 rad $s^{-1}$ oscillatory frequency and 0.5% deformation strain; time sweeps of Poly-AD:rDDD materials; experiments were performed under 6 rad $s^{-1}$ oscillatory frequency and 0.5% deformation strain (FIG. 2C).
Figure 2C:
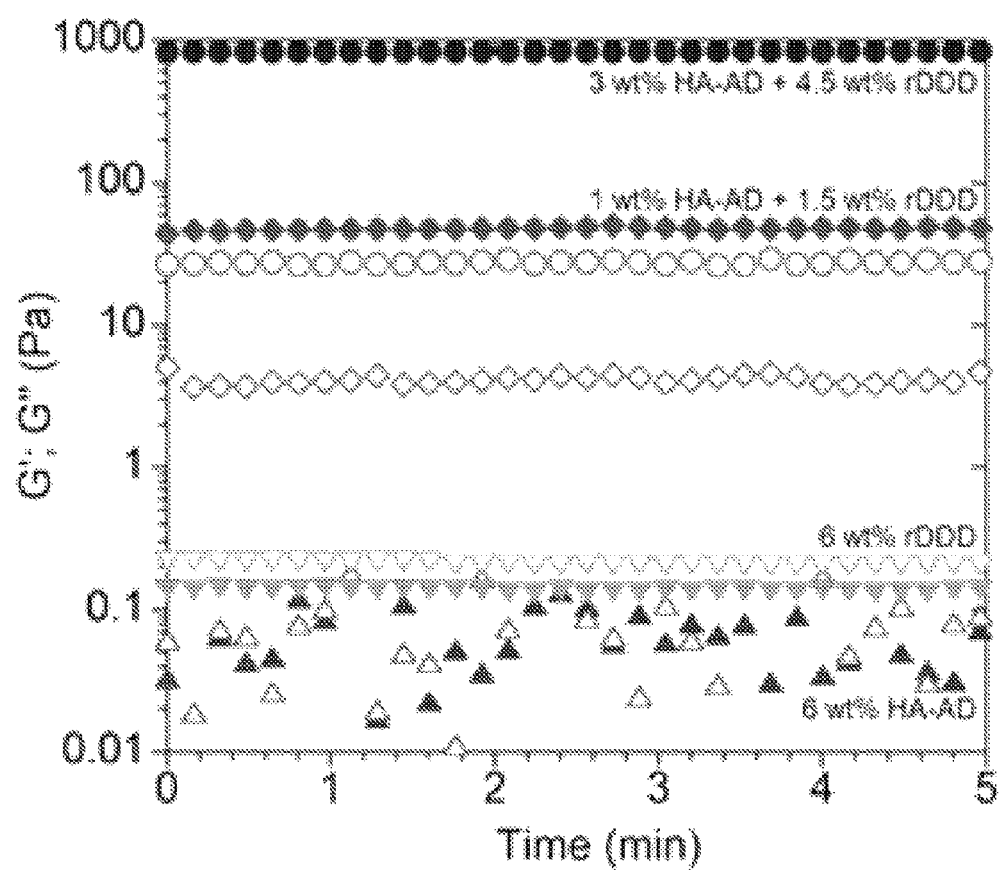

DnL Hydrogel Gelation. The Poly-AD components capable of pH induced self-assembly from conjugating an A-kinase anchoring protein (AKAP) derived polypeptide to polymer backbones are described above (FIG. 2A). The anchoring domain of AKAP is a naturally occurring amphiphilic peptide with affinity to the DDD of protein kinase A (PKA) that can form helical bundles at high concentrations (circular dichroism spectroscopy data detailing protein conformational changes described throughout not shown). AD was engineered by flanking the AKAP domain with hydrophilic and basic amino acids (ESES) that prevent bundle formation via electrostatic repulsion. Poly-AD underwent self-assembly when mixed with rDDD. rDDD domains dimerize (Docking step) and cross-links AD together by forming a type-X tetrameric complex (Locking step) with nanomolar affinity (FIG. 2B). This method of gelation has the advantage of occurring under constant physiological environments, and may be used to encapsulate sensitive cargo under mild conditions.

Engineering DnL Gel Rheology Properties. The elastic properties of DnL gels may be increased by increasing molecular AD valency and subsequent intermolecular network branching (FIG. 2B). Doubling the AD valency of 4aPEG-AD to 8aPEG-AD quantitatively halved gel yield strains (at constant Poly-AD/rDDD wt %, data not shown) due to the decrease of discrete Poly-AD molecules available for network formation by half. Increasing total gel wt % while keeping Poly-AD/rDDD molecular ratios constant increased moduli but had minimal effects on yield strains and material relaxation time, due to increased networking density but unchanged networking architecture (data not shown). Together, these results provided insight between macroscopic properties and the molecular design of materials. Additionally, the flexibility of the DnL system was highlighted by how hydrogels with a large range of physical properties can be constructed by a bottom up approach and changing only the concentration of one component (rDDD) in a two-component rDDD/Poly-AD system (FIG. 3).

Figure 4:
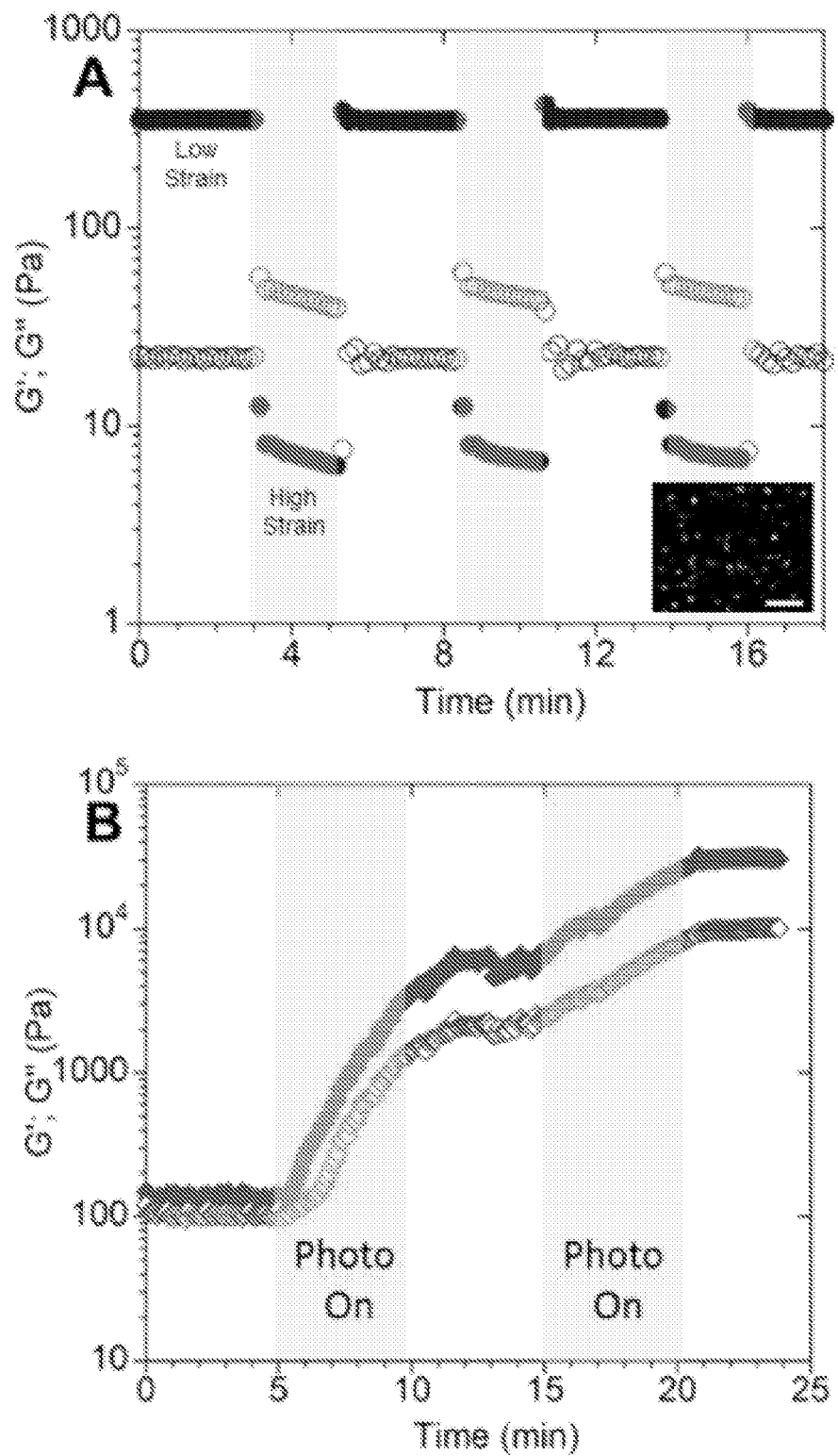
FIG. 4 provides the results of dynamic oscillatory time sweeps and evolution (G', filled shapes; G" open shapes) of 3 wt % 8aPEG-AD-4.5 wt % rDDD alternating between high 500% strain and low 0.5% strain at 6.3 rad/s, and live/dead stain of cells encapsulated and delivered via shearing-thinning through a fine needle (inset, scale bar=50 μM) (FIG. 4A); and time sweep and moduli evolution of 2 wt % MeHA-AKAP-3 wt % rDDD gels after exposure to UV irradiation (FIG. 4B).

DnL Gels for Biomedical Applications. Importantly, these materials flowed as liquids under high strain and rapidly recover to their gel state once shear was removed (FIG. 4A). This shear-thinning and rapidly self-healing property allows DnL gels to be used as injectable scaffolds for cells/drugs delivery. MSCs can be homogenously encapsulated from the 'Dock-and-Lock' mechanism and survive shearing-thinning and flowing through a 21 gauge needle (>90% viability). Polymers that contain additional methacrylate functional groups can still self-assemble into hydrogels with the general 'Dock-and-Lock' mechanism, but were further cross-linked by photopolymerization (FIG. 4B). Secondary photopolymerization cross-linking improves hydrogel stability for use in applications requiring higher elasticity or improved degradation resistance. The modular cross-linking strategy provides the DnL system with the delivery advantages of shear-thinning systems, as well as the stability and robust nature of covalently cross-linked systems.

Figure 5:
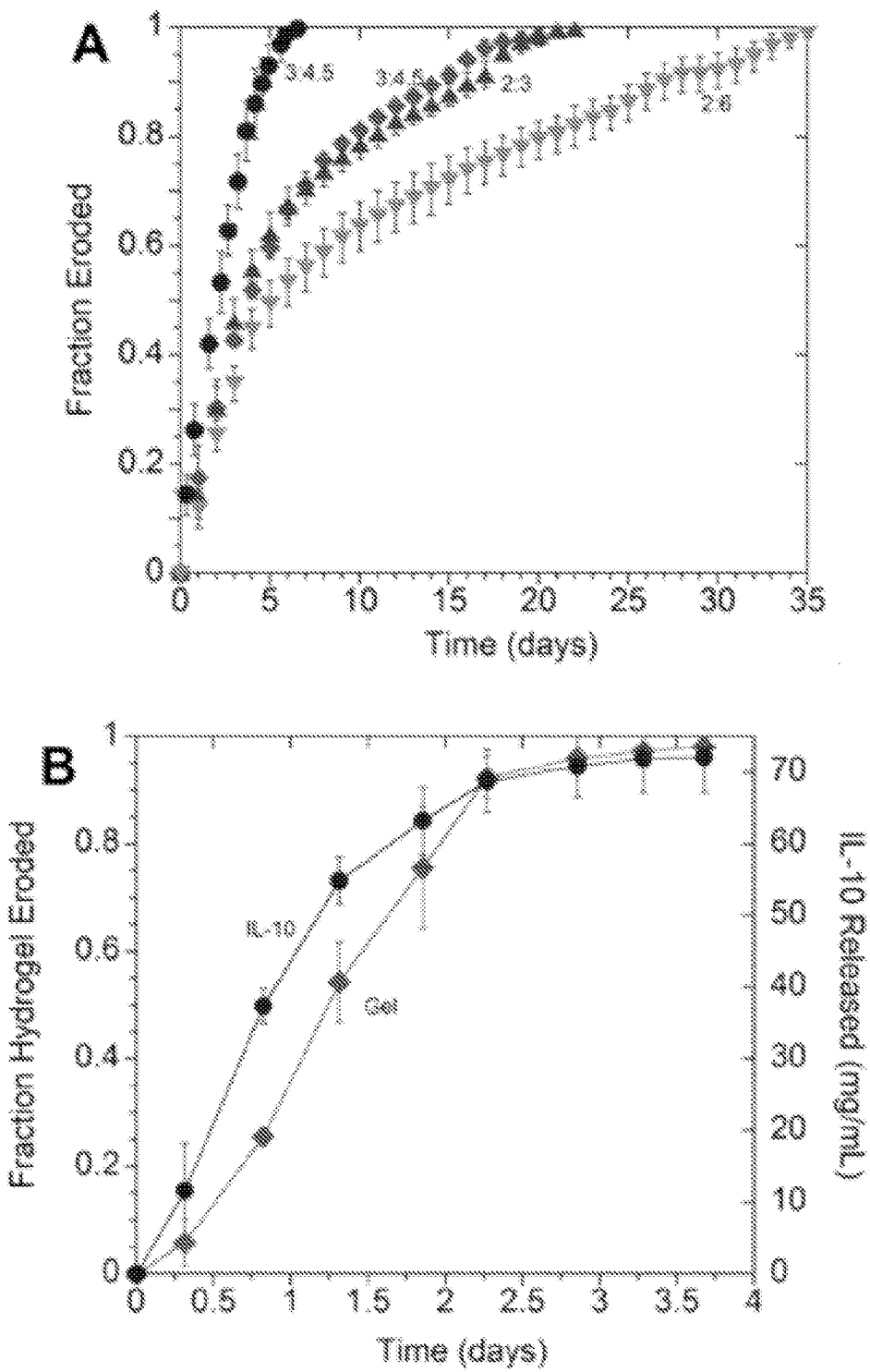
FIG. 5 provides the results of (FIG. 5A) erosion of 4aPEG-AD (3:4.5 circles) and 8aPEG-AD (3:4.5 diamonds, 2:3 triangles, 2:6 inverted triangles) hydrogels at various PEG-AD:rDDD wt % compositions; and erosion of Cy5.5 conjugated 4aPEG-AD gels with concurrent release of encapsulated IL-10 (FIG. 5B).
Figure 8:
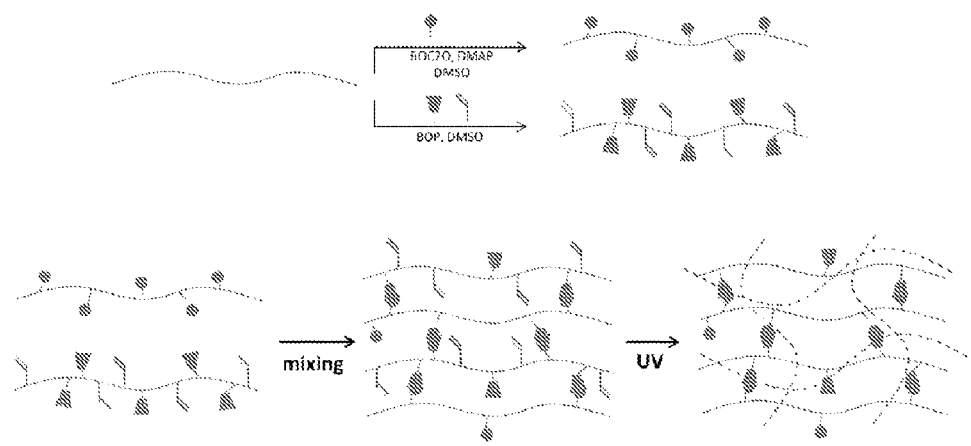
FIG. 8 provides a schematic representation of the concept of dual (non-covalent and secondary chemical covalent) crosslinking as described in the present invention. Top: Synthesis of hyaluronic acid (HA) grafted with the guest molecule 1-adamantane acetic acid (Ad-HA). The HA backbone grafted with the host molecule β-cyclodextran (CD) is also endowed with a methacrylate (Me) to form CD-MeHA. Bottom: Mixing of components is proposed to afford a hydrogel capable of shear-thinning and fast recovery upon cessation of shear. Upon exposure to UV light, photopolymerization is initiated and kinetic chains result in stabilization to form a solid hydrogel.
Figure 9A:
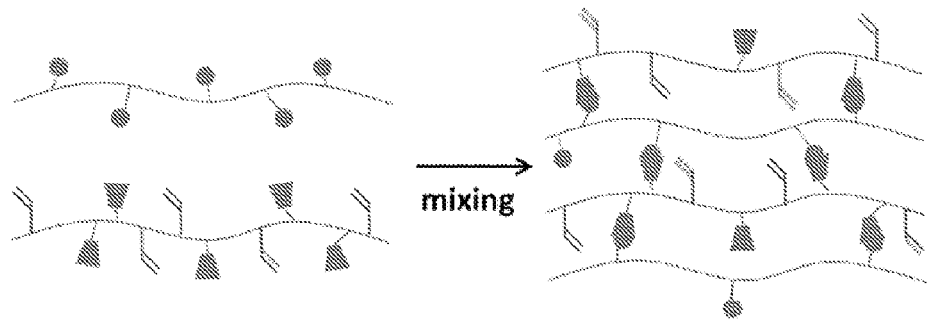
As shown in FIG. 9A. mixing of components affords a hydrogel composed only of dynamic guest-host bonds. As a result, the material is capable of shear-thinning and fast recovery upon cessation of shear.
Figure 9B:
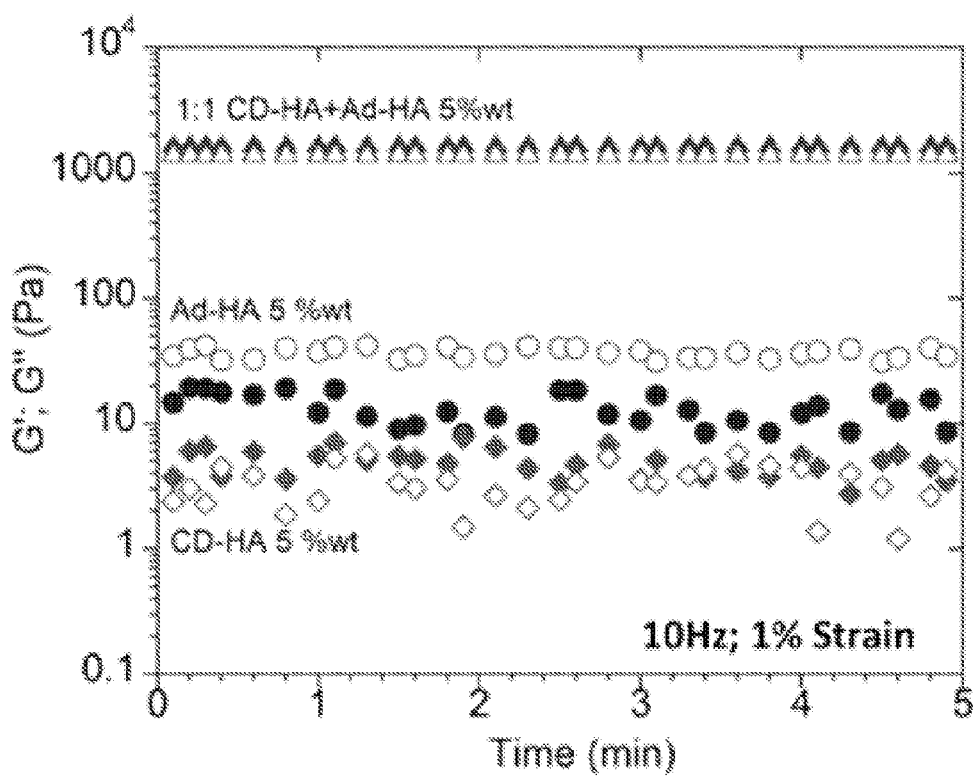
FIG. 9B provides data associated with oscillatory time sweeps of Ad-HA and CD-HA materials in seclusion or following mixing. The solutions of the individual components were, by themselves, lightly viscous solutions as confirmed by oscillatory rheology. Upon mixing to produce gels having CD and Ad functionality in a 1:1 ratio, a pronounced moduli increase is observed and a gel is formed through the network of dynamic guest-host bonds.
Figure 9C:
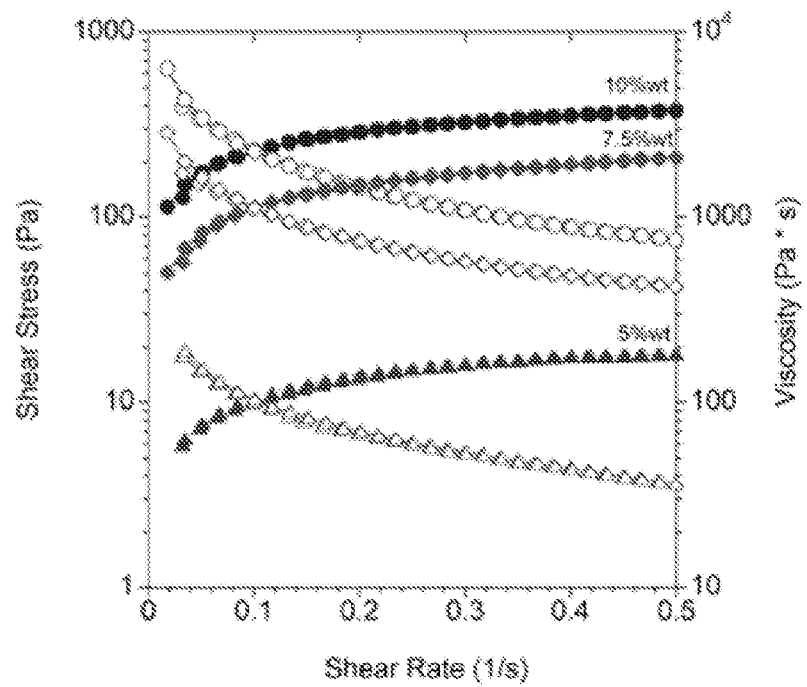
FIG. 9C shows data under ramp-flow conditions, where the viscosity was observed to decrease and shear stress approached a maximum value asymptotically, confirming expected shear-thinning behavior of the guest-host hydrogel.
Figure 9D:
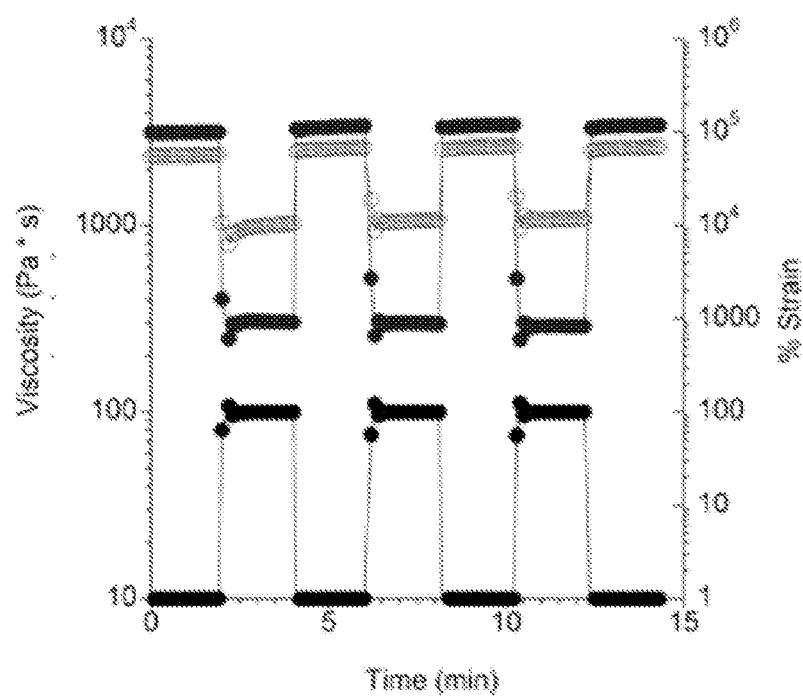
FIG. 9D shows data for shear-thinning and rapid recovery over time from repeated cycles of 2 min low 10% strain and 2 minutes high 100% strain oscillations at 10 Hz. Oscillation of the applied strain showed a transition to a liquid state at high-strain (100% strain) and near immediate recovery to initial mechanics upon onset of low-strain conditions (10% strain).

Like gel rheological properties, gel erosion rates can be tuned by modulating gel components and compositions. Increasing AD molecular valency decreases erosion rates due to increased intermolecular cross-linking (comparing 4aPEG/8aPEG:rDDD gels, FIG. 5A). Varying total gel wt % while retaining constant Poly-AD/rDDD molar ratios had minimal effect on gel erosion rate despite an increased network density, since molecular architecture remained overall similar (comparing 2:3/3:4.5 8aPEG-AD:rDDD gels). Gels with AD/rDDD molar ratios closest to one (2:6 wt %) had the slowest erosion rates. DnL gel erosion rates directly correlate with the release rates of encapsulated protein molecules, such as IL-10 cytokine (FIG. 5B). DnL gels may also be further modified with near-IR fluorescent dyes without interfering with molecular self-assembly.

These gels can be sheared through fine needles into tissue explant, and imaged through thin layers of tissue (such as epithelial layers, data not shown) to monitor gel dispersion and degradation. Together, this demonstrates the system's versatility and ability to tune cell/drug delivery rates from a molecular basis and applicability in biomedical applications.

Example 2

Guest-Host Hydrogels Based on Adamantane-Hyaluronic (Ad-HA) and β-Cyclodextrine-Hyaluronic Acid (CD-HA)

Ad-HA synthesis: Ad-HA was prepared by coupling of 1-adamantane acetic acid (Ad) with HA-TBA (prepared as described in Example 1) through $BOC_2O$/DMAP mediated coupling described previously (see, e.g., E. Tous, J. L., et al., Influence of Injectable Hyaluronic Acid Hydrogel Degradation Behavior on Infarction Induced Ventricular Remodeling, *Biomacromolecules*, 12:4127-4135, 2011). HA-TBA at 2 wt % was dissolved in anhydrous DMSO with Ad and 4-dimethylaminepyridine (DMAP) and allowed to react. The solution was heated to 45° C. and $BOC_2O$ was added via syringe. The reaction was allowed to proceed for 20 hrs, followed by extensive dialysis against deionized $H_2O$, precipitation from excess cold acetone, continued dialysis, and lyophilization to afford the final product. Degree of functionalization was 20% as determined by $^1H$ HMR (see FIG. 11)

CD-MeHA and CD-HA synthesis: CD-MeHA was synthesized by amine coupling of 2-aminoethylmethacrylate (AEMA) and 6-(6-aminohexyl)amino-6-deoxy-62-cyclodextrin (CD-HDA) to the TBA salt of hyaluronic acid (HA-TBA). CD-HDA was prepared by methods similar to those previously described in E. Kaya, et al., Synthesis and Characterization of Physical Crosslinking Systems Based on Cyclodextrin Inclusion/Host-Guest Complexation, *Journal of Polymer Science*: Part A: Polymer Chemistry, 48:581-592. 2010). Briefly, reaction was accomplished by dissolving HA-TBA in anhydrous DMSO at 2 wt % with CD-HDA, AEMA, hydroxyquinone (HQ, radical scavenger to prevent polymerization), and Benzotriazole-1-yl-oxy-tris-(dimethylamino)-phosphonium hexafluorophosphate (BOP, amine coupling reagent). Extensive dialysis, filtration, and lyophilization afforded the final product, having a degree of functionalization of 20% for both methacrylate and cyclodextrin functional groups as determined by $^1H$ NMR. CD-HA was prepared by identical methodology, where AEMA and HQ are neglected in the reaction. The degree of functionalization of cyclodextrin determined to be 20% by $^1H$ NMR.

Figure 11:
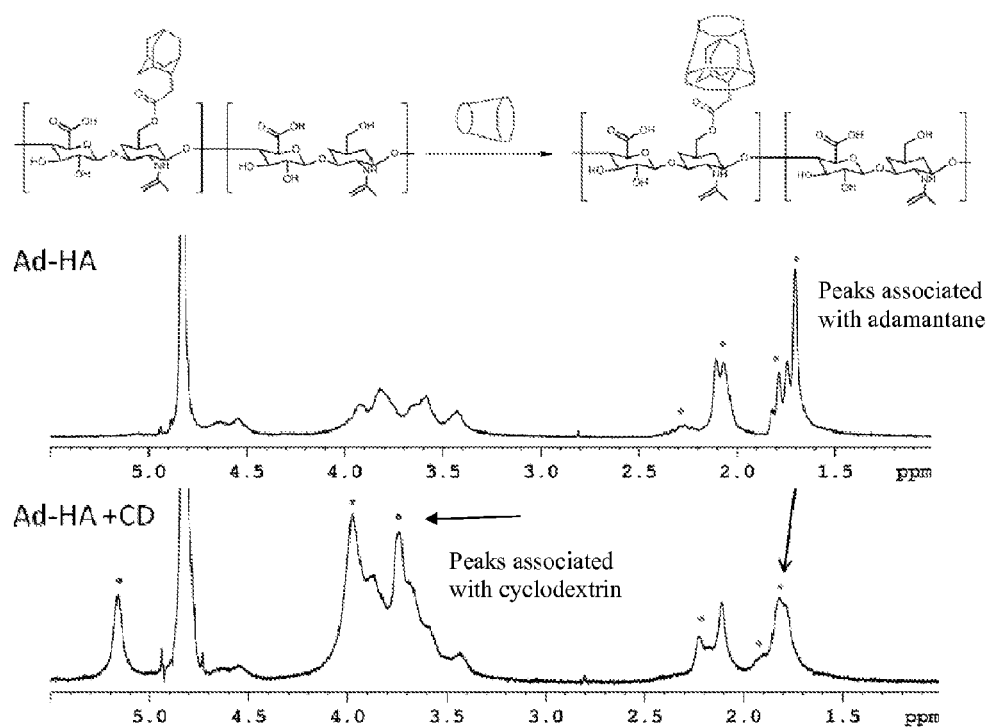
FIG. 11 illustrates the interaction of individual components with the complementary guest or host group was confirmed by $^1$H NMR. See Example 2.

Guest-Host Hydrogel characterization. The interaction of individual components with the complementary guest or host group was confirmed by $^1H$ NMR. (FIG. 11) Ad-HA (5.0 mg) was dissolved in 0.75 mL $D_2O$ with or without the addition of 2 mg CD. Analogous samples were prepared for CD-HA containing Ad. Observed shifts in the guest-molecule spectra confirm interaction, as is standard practice in the field. With the inclusion of CD, shifts corresponding to the guest molecule combined and shifted slightly up-field in the spectra, as indicated in FIG. 11. Observed shifts are consistent with formation of the guest-host complex. Analogous examination of CD-HA containing soluble Ad showed similar trends.

For rheological evaluation, Guest and Host components were separately dissolved in PBS to prepare stock solutions. To initiate gelation self-assembly, separate components were mixed together to afford a 1:1 ratio of CD and Ad functionality. Dynamic oscillatory time, frequency and strain sweeps were performed on materials using cone and plate rheometry (AR2000, Texas Instruments). Photopolymerization 'stabilization' cross-linking was initiated by UV radiation using IRGACURE™ I2959 photo-initiator at 0.05 wt % in the hydrogels.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A settable, shear-thinning supramolecular hydrogel comprising a hydrophilic polymer network comprising a plurality of pairs of host-polymers and guest-polymers, each host-polymer and guest-polymer pair linked through a coupled pair of host and guest moieties, wherein each of the host-polymers and guest-polymers separately comprise at least one set of chemical moieties, which are capable of reacting with each other in at least one chemical covalent cross-linking reaction.

2. The hydrogel of claim 1, wherein each of the host-polymers and guest-polymers separately comprises at least two sets of chemical moieties, wherein each set of chemical moieties is capable of independently reacting together in separate chemical covalent cross-linking reactions.

3. The hydrogel of claim 1, wherein the chemical covalent cross-linking reaction is triggerable by an internal or external stimulus.

4. The hydrogel of claim 3, wherein at least one set of chemical moieties is capable of participating in a chemical covalent cross-linking reaction within the hydrogel when triggered by an external stimulus, wherein the external stimulus is light.

5. The hydrogel of claim 4, further comprising a photo-initiator.

6. The hydrogel of claim 3, wherein at least one set of chemical moieties is capable of participating in a chemical covalent cross-linking reaction within the hydrogel when triggered by an external stimulus, wherein the external stimulus is microwave radiation.

7. The hydrogel of claim 3, wherein at least one set of chemical moieties is capable of participating in a chemical covalent cross-linking reaction within the hydrogel when triggered by an external stimulus, wherein the external stimulus is a change in pH or temperature, a free radical initiator, or a combination thereof.

8. The hydrogel of claim 7, further comprising a thermal radical initiator.

9. The hydrogel of claim 3, wherein at least one set of chemical moieties is capable of participating in a chemical covalent cross-linking reaction within the hydrogel when triggered by an internal stimulus, the internal stimulus being the formation of the hydrogel.

10. The hydrogel of claim 1, wherein one or both of the host-polymers and guest-polymers comprises an agarose, alginate, RGD-modified alginate, amylase, amylpectin, cellularose, chitosan, collagen, dextran, fibrin, gelatin, glycogen, heparin, hyaluronic acid, poly(acrylamide), poly(β-aminoester), poly(caprolactone), matrigel, multi-arm polyethylene glycol, poly-hydroxyethyl acrylate, poly(hydroxyethyl methacrylate), poly(N-isopropylacrylamide), poly(glycolic acid), poly(lactic acid), poly(lactic acid-glycolic acid), oligo(poly(ethylene glycol)fumarate), poly(vinyl alcohol), or a poly(vinyl acid).

11. The hydrogel of claim 1, wherein one or both of the chemical moieties is attached to the respective host-polymer and guest-polymer by a linking group.

12. The hydrogel of claim 11, wherein the linking group is biodegradable under physiological conditions.

13. The hydrogel of claim 1, further comprising a moiety capable of fluorescing or phosphorescing after exposure to light.

14. The hydrogel of claim 1, wherein one or both of the chemical moieties is incorporated into the backbone of the respective host-polymer and guest-polymer.

15. The hydrogel of claim 1, wherein the at least one covalent crosslinking reaction is a condensation reaction, Michael addition, or a free radical polymerization reaction.

16. The hydrogel of claim 1, wherein at least one set of chemical moieties capable of participating in the at least one covalent chemical crosslinking reaction comprises an acrylate, acrylamide, optionally protected alcohol, aldehyde, alkyne, optionally protected amine, anhydride, azide, carboxy, epoxy, ester, hydrazide, ketone, maleimide, methacrylate, styrenyl, optionally protected thiol, or vinyl or vinyl sulfone group.

17. The hydrogel of claim 1, wherein a product of the at least one chemical covalent cross-linking reaction is an ester, ether, amide, hydrozone, polyacrylate, polymethacrylate, thioamide, thioester, thioether, or urethane.

18. The hydrogel of claim 1, wherein the host-polymer comprises a first hydrophilic polymer comprising a plurality of moieties each having a hydrophobic cavity and the guest-polymer comprises a second hydrophilic polymer comprising a plurality of hydrophobic anchoring moieties.

19. The hydrogel of claim 18, wherein the moiety capable of providing a hydrophobic cavity comprises a calixarene, a cucurbituril, or a cyclodextrin.

20. The hydrogel of claim 18, wherein the moiety capable of providing a hydrophobic cavity comprises an optionally substituted cyclodextrin.

21. The hydrogel of claim 18, wherein the hydrophobic anchoring moiety comprises a linear, branched, cyclic, or polycyclic $C_{6\text{-}20}$ hydrocarbon, $C_{6\text{-}20}$ aryl or alkylaryl, hetero or alkylaromatic hydrocarbon moieties.

22. The hydrogel of claim 18, wherein the coupled pair of pair of host and guest moieties comprises an alpha-cyclodextrin/hexyl group pair, an alpha-cyclodextrin/polyethylene oxide group pair, a beta-cyclodextrin/adamantane group pair, a beta-cyclodextrin/cyclohexyl group pair, a beta-cyclodextrin/benzyl group pair, a gamma-cyclodextrin/cyclodecyl group pair, a cucurbituril/hexanediamine group pair, or a cucurbituril/spermine group pair.

23. The hydrogel of claim 18, wherein at least one of the first or second hydrophilic polymers comprise hyaluronic acid.

24. The hydrogel of claim 23, wherein the first and second hydrophilic polymers both comprise hyaluronic acid.

25. The hydrogel of claim 18, wherein each of the first and second hydrophilic polymers separately comprises at least two sets of chemical moieties, wherein each set of chemical moieties is capable of independently crosslinking when subjected to a separate stimulus.

26. The hydrogel of claim 1, wherein the hydrophobic anchoring moiety is an adamantane.

27. The hydrogel of claim 1, wherein the host-polymer comprises a first hydrophilic polymer comprising a plurality of moieties linked thereto, each having a hydrophilic cavity; and the guest-polymer comprises a second hydrophilic polymer having a plurality of hydrophilic anchoring moieties linked thereto.

28. A cured hydrogel, where the hydrogel of claim 1 has been cross-linked by the reaction of the at least one set of the chemical moieties.

29. The cured hydrogel of claim 28, further comprising a pharmaceutically active drug or nutraceutical, a population of cells, nanoparticle, quantum dot, magnetic material, or combination thereof.

30. The hydrogel of claim 1, wherein the hydrogel is adapted to be medically acceptable for use in a mammal.

31. The hydrogel of claim 30, where the mammal is human.

32. The hydrogel of claim 1, wherein at least one set of chemical moieties is capable of participating in a chemical covalent cross-linking reaction spontaneously within the hydrogel, without the need for triggering by an external stimulus.

33. The hydrogel of claim 1, wherein at least one of the host-polymers and guest-polymers comprise an agarose, alginate, RGD-modified alginate, amylase, amylpectin, cellularose, chitosan, collagen, dextran, fibrin, gelatin, glycogen, heparin, hyaluronic acid, poly(acrylamide), poly(β-aminoester), poly(caprolactone), matrigel, multi-arm polyethylene glycol, poly-hydroxyethyl acrylate, poly(hydroxyethyl methacrylate), poly(N-isopropylacrylamide) poly(glycolic acid), poly(lactic acid), poly(lactic acid-glycolic acid), oligo(poly(ethylene glycol)fumarate), poly(vinyl alcohol), or a poly(vinyl acid), each of the host-polymer and guest-polymer being linked by a coupled pair of host and guest moieties comprising substituted cyclodextrin and adamantane, wherein each of the host-polymers and guest-polymers separately comprise at least one set of chemical moieties capable of spontaneously crosslinking by a Michael addition reaction.

34. A method of preparing a controlled or sustained release formulation of a pharmaceutically active drug, nutraceutical, or cell population in a patient, said method comprising introducing into the patient a composition comprising a hydrogel of claim 1 and a pharmaceutically active drug, nutraceutical, or cell population.

35. The method of claim 34, further comprising initiating at least one chemical covalent crosslinking reaction.

36. A method of preparing a controlled or sustained release formulation of a pharmaceutically active drug, nutraceutical, or cell population in a patient, said method comprising introducing into a patient the composition comprising a hydrogel of claim 2 and a pharmaceutically active drug, nutraceutical, or cell population.

37. The method of claim 36, further comprising initiating at least one chemical covalent crosslinking reaction.

38. The method of claim 36, wherein the hydrogel is introduced into the patient by way of a needle, catheter, or cannula.

* * * * *